United States Patent
Werber et al.

(10) Patent No.: US 9,814,746 B2
(45) Date of Patent: *Nov. 14, 2017

(54) METHOD OF TREATMENT UTILIZING AN ACELLULAR AMNION DERIVED THERAPEUTIC COMPOSITION

(71) Applicant: Amnio Technology LLC, Phoenix, AZ (US)

(72) Inventors: Bruce Werber, Phoenix, AZ (US); Christian Beaudry, Phoenix, AZ (US); Terrell Suddarth, Winchester, TN (US)

(73) Assignee: Amnio Technology LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,889

(22) Filed: Sep. 14, 2015

(65) Prior Publication Data

US 2016/0199417 A1   Jul. 14, 2016

Related U.S. Application Data

(63) Continuation-in-part of application No. 14/593,415, filed on Jan. 9, 2015, now Pat. No. 9,132,156, and a continuation-in-part of application No. PCT/US2015/019294, filed on Mar. 6, 2015, and a continuation-in-part of application No. PCT/US2015/019318, filed on Mar. 6, 2015, and a continuation-in-part of application No. PCT/US2015/019311, filed on Mar. 6, 2015.

(51) Int. Cl.

| | |
|---|---|
| *A61K 35/50* | (2015.01) |
| *A61K 9/00* | (2006.01) |
| *A61K 9/06* | (2006.01) |
| *A61Q 19/00* | (2006.01) |
| *A61Q 19/08* | (2006.01) |
| *A61K 8/98* | (2006.01) |
| *A61K 35/28* | (2015.01) |
| *A61K 35/35* | (2015.01) |
| *A61K 35/44* | (2015.01) |

(52) U.S. Cl.
CPC ............. *A61K 35/50* (2013.01); *A61K 8/982* (2013.01); *A61K 9/0014* (2013.01); *A61K 9/0019* (2013.01); *A61K 9/0034* (2013.01); *A61K 9/0046* (2013.01); *A61K 9/0048* (2013.01); *A61K 9/0053* (2013.01); *A61K 9/06* (2013.01); *A61K 35/28* (2013.01); *A61K 35/35* (2013.01); *A61K 35/44* (2013.01); *A61Q 19/00* (2013.01); *A61Q 19/08* (2013.01); *A61K 2800/74* (2013.01)

(58) Field of Classification Search
None
See application file for complete search history.

(56) References Cited

U.S. PATENT DOCUMENTS

| | | | | |
|---|---|---|---|---|
| 2004/0057938 A1* | 3/2004 | Ghinelli | ............... | A61K 35/48 424/93.7 |
| 2008/0286378 A1* | 11/2008 | Behrens | ............... | A61K 35/50 424/528 |
| 2015/0216912 A1* | 8/2015 | Koob | ................. | A61K 35/50 424/93.7 |

OTHER PUBLICATIONS

Ozgenel et al, Effects of human amniotic fluid on cartilage regeneration from free perichondrial grafts in rabbits The British Association of Plastic Surgeons, 2004, vol. 57, pp. 423-428.*

* cited by examiner

Primary Examiner — Allison Fox
(74) Attorney, Agent, or Firm — Invention To Patent Services; Alex Hobson

(57) ABSTRACT

Acellular amnion derived therapeutic compositions are described having a number of various compositional embodiments. An acellular amnion derived therapeutic composition has essentially no live or active amniotic cells. The amniotic cells may be destroyed, and the cells and cell debris may be removed from the acellular amnion derived therapeutic composition. An acellular amnion derived therapeutic composition may comprise micronized placental tissue particles, and/or amniotic fluid. An acellular amnion derived therapeutic composition may be a dispersion of micronized amniotic membrane combined with a fluid, such as plasma, saline, amniotic fluid, combinations thereof and the like. An acellular amnion derived therapeutic composition may be combined with a matrix component to form a composite. An acellular amnion derived therapeutic composition may be used in conjunction with a composition comprising viable cells, such as stem cells.

37 Claims, 20 Drawing Sheets

METHOD OF TREATMENT UTILIZING AN ACELLULAR AMNION DERIVED THERAPEUTIC COMPOSITION

CROSS REFERENCE TO RELATED APPLICATIONS

This application is a continuation in part of U.S. patent application Ser. No. 14/593,415, filed on Jan. 9, 2015 and currently pending, which claims the benefit of U.S. provisional patent application No. 62/012,394, filed on Jun. 15, 2014, and this application claims the benefit of PCT/US2015/035746, filed on Jun. 15, 2015; all of which are entitled Acellular Amnion Derived Therapeutic Compositions and the entirety of which are incorporated by reference herein; this application is also a continuation in part of PCT/US2015/019294, PCT/US2015/019318 and PCT/US2015/019311, all filed on Mar. 6, 2015 and entitled Amnion Derived Therapeutic Compositions and Methods of Use.

BACKGROUND OF THE INVENTION

Field of the Invention

The present invention relates to therapeutic compositions comprising amnion derived acellular materials and methods of use.

Background

Amnion derived materials are being used to treat a wide array of conditions such as to promote tissue healing. A widely known practice is to treat a treatment location with amniotic material comprising live amniotic cells, including amniotic stem cells in some case. This requires special handling, as the amniotic cells are fragile and will become inactive if not maintained in a proper condition, including temperature.

Amniotic material that is free of amniotic cells or that comprises no live or active amniotic cells may be a useful treatment composition and would require less stringent handling.

SUMMARY OF THE INVENTION

The invention is directed to a therapeutic composition comprising amnion derived material that is free of live, or viable cells including amniotic stem cells. An acellular amnion derived material includes at least one of the following: amniotic membrane, amniotic fluid, and/or the following derived from the amniotic membrane and/or amniotic fluid; proteins including growth factors and cytokines, extracellular proteins such as annexin, fibronectin, vitronectin, collagen and the like. An acellular amnion derived therapeutic composition may comprise amniotic stem cells that are not live or active. In some cases, the cell wall, also known as cell membrane, of an amniotic stem cell is ruptured and in other embodiments, essentially all complete and intact amniotic cells are removed from the acellular amnion derived therapeutic composition. In some embodiments, an amnion material, comprising growth factors and/or cytokines, is concentrated in a therapeutic composition, whereby the concentration is higher than in the received donor tissue or fluid. In other embodiments, a therapeutic composition, as described herein, comprises amnion materials, such as growth factors and/or cytokines, that are diluted or about the same concentrated as received from a donor. Additional materials including, but not limited to, carriers, diluents or a second therapeutic composition may be included with the amnion derived therapeutic composition. A second composition may comprise live or viable cells, including stem cells. Specific protein markers may be identified and measured to determine the concentration of the amnion derived components with a therapeutic composition.

An acellular amnion derived composition is a material derived from amnion material but contains essentially no live amniotic cells. In an exemplary embodiment, an amnion derived acellular composition comprises no live or active amniotic derived cells. In another embodiment, an acellular amnion derived therapeutic composition comprises essentially no intact amniotic derived cells. In yet another embodiment, an acellular amnion derived therapeutic composition is decellularized and comprises a reduced quantity of cells, such as no more than about five percent, no more than about three percent, no more than about two percent, or no more than about one percent of an original cell concentration. As described herein, during the micronizing of the amniotic membrane, some cells may be fractured, leaving cell fragments and essentially no intact cells. An acellular amnion derived therapeutic composition may comprise live cells that are not derived from amnion however.

An acellular material, as used herein, is defined as a material having essentially no viable cells wherein no more than 1% of the total number of cells in the material are viable. In an exemplary embodiment, an acellular composition contains no viable cells. In an exemplary embodiment, an acellular composition is essentially cell free. Essentially cell free, as used herein, is defined as a composition that contains essentially no cells, wherein the cells have been removed or destroyed through cryo-fracturing, for example.

An acellular amnion derived therapeutic composition may comprise amniotic membrane and/or collagen to provide a scaffold for native cells to grow into. In an exemplary embodiment, an acellular amnion derived therapeutic composition comprises micronized particles of amniotic membrane. In still another embodiment, an acellular amnion derived therapeutic composition comprises a concentrated amniotic fluid. Amniotic stem cells may be present in an acellular amnion derived therapeutic composition, but they are not active and may be ruptured or otherwise physically compromised. Any of the amniotic derived materials described herein may be concentrated, by removal of water or other fluids and may have a concentration that is at least about 10% higher, at least about 25% higher, at least about 50% higher, at least about 100% higher, at least about 200% higher, at least about 400% higher than a concentration as received in the donor material. As described herein, an amniotic derived composition may also be diluted or provided with components concentrations that are about the same as those as found in donor materials.

Amniotic cells including amniotic stem cells may be removed and/or made inactive. Amnion material, including amniotic membrane and amniotic fluid may be decellularized, made essentially acellular as defined herein, through any effective means including, but not limited to, centrifugation, lysis, enzymatic digestion, freezing, filtration, precipitation, flow sorting, sonication and through chemical treatment or any other process known in the art. Centrifugation may be used to reduce the number of cells within amniotic material or fluid. Amniotic fluid may be decellularized through centrifugation to reduce the number of cells down to about 750,000 or less intact cells per ml of amniotic fluid, about 450,000 or less intact cells per ml of amniotic fluid, about 300,000 or less intact cells per ml amniotic fluid, or about 150,000 or less intact cells per ml of amniotic fluid.

An as received amniotic fluid from a donor may comprise about 15 million cells per milliliter before centrifugation and therefore the cell concentration may be reduced to about five percent or less, about three percent or less, about two percent or less, or about one percent or less of the original cell concentration. Cells may be destroyed to produce cell fragments by the addition of chemicals that cause the cell wall of the amniotic cells to rupture, thereby making them inactive. The amniotic cells may be removed through sonication or filtration, for example. In other embodiments, the amniotic cells are made inactive but the cells or cell debris may be left in the amnion derived therapeutic composition.

An acellular amnion derived therapeutic composition may be provided in a form for direct application to a treatment location, such as by topical application, spraying or use of an eye dropper, for example. In other embodiments, an acellular amnion derived therapeutic composition is provided with an applicator such as a sponge, gauze, or a biological applicator, such as an amniotic membrane or composite incorporating amniotic membrane. In still another embodiment, an acellular amnion derived therapeutic composition may be coated onto an applicator in specific locations to enhance healing, for example.

Any suitable treatment protocol may be used to administer an acellular amnion derived therapeutic composition to a treatment location. In one embodiment, an acellular amnion derived therapeutic composition is applied along with or subsequent to the application of an amniotic composition comprising live amniotic stem cells. For example, a therapeutic dose of live amniotic stem cells may be applied to a treatment location and a separate dose of acellular amnion derived therapeutic composition may be applied to the same treatment location. In addition, subsequent applications of an acellular amnion derived therapeutic composition may be applied to the treatment location to enhance the effectiveness of the treatment.

In another treatment protocol, cells, including in some embodiments, stem cells, derived from a secondary source may be applied to a treatment location and an acellular amnion derived therapeutic composition may also be applied to said treatment location. The secondary source may be from a patient and the stem cells may be derived from bone marrow, adipose tissue or a stromal vascular fraction (SVF), for example. In still another embodiment, live stem cells derived from a secondary source, such as a stromal vascular fraction, may be added to an acellular amnion derived therapeutic composition to create an acellular amnion derived therapeutic composition comprising live non-amnion derived stem cells and an acellular amnion derived component. In this manner, the effectiveness of stem cells derived directly from the patient or a secondary source may be improved by the application of an acellular amnion derived therapeutic composition. The additional growth factors, cytokines and scaffolding materials applied to the treatment location along with the live stem cells may greatly increase the healing and regenerative effect It is to be understood that the non-amnion active stem cells may be derived from any suitable location when applied with or combined with an acellular amnion derived therapeutic composition. An amnion derived composition, may be combined or mixed with a platelet rich plasma (PRP) and applied to a treatment location as described herein. For example, an amnion derived fluid composition comprising amniotic fluid and/or placental tissue particles may be mixed with PRP and used as a topical treatment composition, injectable treatment composition, intravenous treatment composition, oral treatment composition or used in an intraoperative procedure. In an exemplary embodiment, a therapeutic composition, as described herein, combined with PRP is injected into a joint, such as the knee, injected into the scalp to promote hair growth, or used for cosmetic application, such as injections to reduce wrinkles.

In an exemplary embodiment, a SVF comprising live stem cells derived from the tissue of a patient, for example, may be combined with micronized amniotic membrane to form a therapeutic composition for said patient. The SVF may contain any of the following preadipocytes, mesenchymal stem cells (MSC), endothelial progenitor cells, T cells, B cells and mast cells as well as adipose tissue macrophages. In some embodiments, an acellular amnion derived therapeutic composition is doped with progenitor cells and the progenitor cells may be multipotent progenitor cells and/or pluripotent progenitor cells. Progenitor cells may be derived from a patient to be treated, such as from a stromal vascular fraction. Vascular fraction cells and/or progenitor cells may be included with a therapeutic composition to further improve effectiveness. Progenitor cells may be autologous or allogeneic.

An acellular amnion derived therapeutic composition may require cryopreservation as do compositions comprising viable amnion cells. In some embodiments, the acellular amnion derived therapeutic composition comprises no live or active stem cells and therefore, there is no requirement to preserve the composition to ensure viability of the stem cells upon thawing. An acellular amnion derived therapeutic composition may be able to be kept at room temperature or refrigerated for long periods of time prior to administering to a treatment location.

In one embodiment, a therapeutic composition, as described herein, comprises an acellular amniotic fluid that may be applied directly to a treatment location including topically, intravenously, intraoperatively, orally and the like. In addition, a therapeutic composition comprising an acellular amniotic fluid may be combined with a carrier fluid, such as saline, hydrogel, oils, and the like. Additional non-amniotic fluid derived cells may be added to an acellular amniotic fluid, including progenitor cells, stromal vascular fraction cells and the like. An exemplary process for preparing a therapeutic composition, includes decellularizing an amniotic fluid to produce an acellular amniotic fluid as described herein, and in some cases filtering the acellular amniotic fluid to remove debris. An acellular amniotic fluid may be concentrated to reduce the liquid content and to increase a solids concentration. Concentration may be performed through centrifugation, air drying, exposure to vacuum, exposure freeze-drying or any methods for concentration a fluid known in the art. The fluid content, as determined through TGA, for example, may be no more than about 75%, no more than about 50%, no more than about 25%, no more than about 10% and in some cases there may substantially no liquid having fluid content of no more than 2%. Subsequent to concentrating the acellular amniotic fluid, the acellular amniotic fluid may be rehydrated or combined with a carrier fluid to produce an acellular amniotic fluid having a concentration of components, such as proteins, cytokines, and growth factors that is greater, less than or substantially equal to the concentration of these components in an amniotic fluid received from a donor, or in an acellular amniotic fluid prepared as described herein, such as after decellularization and/or filtering.

In an exemplary embodiment, viable cells may be added to an acellular amniotic fluid to produce a therapeutic fluid component, as described herein. Cells may be derived from amnion materials including placental tissue, amniotic membrane and/or amniotic fluid, cells derived from a stromal vascular fraction and the like. In an exemplary embodiment, amnion derived cells that were removed from the amniotic fluid and/or amniotic membrane during the process of decellularization may be added back to the acellular amniotic fluid, such as during the rehydration step. In this way, a specific and controlled viable cell concentration may be produced, thereby producing a therapeutic composition with known concentrations of viable cells. A therapeutic composition comprising a known and controlled viable cell concentration may provide more effective treatment efficacy.

An acellular amniotic fluid or therapeutic fluid component, as described herein, may be combined with a support layer or matrix component, as described herein, including, but not limited to, polymer matrix material including a bioresorbable or fluoropolymer membrane, and/or an amniotic membrane. An acellular amniotic fluid or therapeutic fluid component may be coated onto or imbibed into a support layer to produce a therapeutic composite. An acellular amniotic fluid or therapeutic fluid component may comprise a plurality of micronized placental tissue, such as amniotic membrane particles which may be acellular, as described herein. The concentration of the micronized placental tissue particles may comprise viable amniotic membrane cells or additional viable cells may be added to the composition, including non-amnion derived viable cells, or viable cells that were removed from the amniotic fluid or membrane during prior processing.

In an exemplary embodiment, an acellular amniotic fluid is combined with a support, matrix component or amniotic membrane to produce a therapeutic membrane or composite and in a preferred embodiment, the acellular amniotic fluid is a concentrated acellular amniotic fluid having a higher concentration of proteins and growth factors than received in the donor material. In another exemplary embodiment, a therapeutic fluid component comprising acellular amniotic fluid and micronized amniotic membrane particles is combined with support or matrix component such as an amniotic membrane to produce a therapeutic membrane or therapeutic composite. The higher concentration of proteins and growth factors, for example, may provide greater treatment effectiveness. In still another exemplary embodiment, a therapeutic fluid component comprising an acellular amniotic fluid having viable cells added to the acellular amniotic fluid and micronized placental tissue particles. The additional viable cells added in this embodiment, such as stem cells may provide greater treatment effectiveness. This therapeutic fluid component may be combined with an amniotic membrane to produce a therapeutic composite. In particular, viable cells added to an acellular amniotic fluid may be cells removed from the amniotic fluid and/or membrane during the decellularization process as described herein. In this manner, the therapeutic composition is derived from a single donor and may comprise a therapeutic fluid component with a greater concentration of viable cells and/or proteins, for example, than the concentration of the donor material.

A therapeutic fluid component and/or a therapeutic composition comprising micronized placental tissue particles, may be combined with a support or matrix component, such as an amniotic membrane through methods of combining including coating, soaking, vacuum imbibing, electrophoresis, coating and drying with forced air to create a gradient of composition of components through the thickness of the amniotic membrane and the like. A therapeutic fluid or composition, as described herein may be coated only on one side of a support or amniotic membrane, or imbibed at least partially into the thickness of the amniotic membrane. In an exemplary embodiment, there is a gradient of concentration of proteins derived from the therapeutic fluid or therapeutic composition through the thickness of the amniotic membrane or support. In still another embodiment, viable cells are combined with a therapeutic fluid or composition before application or combining with a support or amniotic membrane. Again, the concentration of the viable cells may be uniform throughout the thickness or may have a gradient from one side to the opposing side, or through the thickness of the support. In an exemplary embodiment, the therapeutic composition or fluid is coated on one or both sides of the support, wherein substantially all of the therapeutic fluid or composition is configured on the surface, such a plurality of placental tissue particles.

In one embodiment an acellular amnion derived therapeutic composition, as described herein, comprises particles of micronized amniotic membrane and/or non-active or destroyed amniotic stem cells. In one embodiment, an acellular amnion derived therapeutic composition is a dispersion of micronized amniotic membrane combined with a fluid, such as plasma, saline, amniotic fluid, combinations thereof and the like. In one embodiment, the acellular amnion derived therapeutic composition consists essentially of a mixture of micronized placental tissue particles combined with amniotic fluid. In one embodiment, the acellular amnion derived therapeutic composition consists essentially of a mixture of micronized amniotic membrane particles, amniotic fluid and saline. An acellular amnion derived therapeutic composition may comprise a concentration of proteins including growth factors and cytokines that can be equal to, lower or higher than the concentration as received in the donor material.

The micronized amniotic membrane may comprise hydrated mammalian amniotic tissue having a percent hydration that is greater than zero, at least about 25%, at least about 50%, at least about 75% by weight or any range between the concentrations provided. Proteins can be more stable in concentrated compositions with lower percent hydrations. Amniotic membrane maintained in a hydrated state may provide for more regenerative properties. The particles in the therapeutic composition as described herein may consist essentially of amniotic membrane and be essentially free of chorion. The amnion layer may be removed from the chorion prior to processing. In one embodiment, the placental tissue particles consist essentially of amniotic membrane particles wherein the amnion layer consists of the epithelium, fibroblast layer and basement membrane compact layer. The placental tissue particles may consist essentially of any of these discrete amnion layers or any combination thereof. In an exemplary embodiment, the placental tissue particles consist essentially of epithelium wherein the concentration of the epithelium is about 70% or more, for example. The particles consisting essentially of epithelium may comprise stem cells and tissue that may substantially surround the stem cells. The amniotic membrane particles may be derived from dehydrated and/or decellularized amniotic tissue. An amniotic membrane may be cryo-fractured, such as with a blunt object to minimize shear and damage to tissue, thereby improving therapeutic effectiveness. Particles of amniotic membrane may have any suitable particle size, average particle size and particle size distribution. For example, the amniotic membrane derived particles, or micronized particles, may have a particle size, or an average particle size of no more than about 1000 µm, no more than about 100 µm, no more than about 75 µm, no more than about 50 µm, no more than about 25 µm, no more than about 10 µm and any range between and including the average particle sizes provided. The average particle size of the placental tissue particles can be determined through any suitable method, including image analysis, whereby a therapeutic composition is dried and imaged using a scanning electron micrograph (SEM). The amniotic membrane derived particles may have an irregular shape and in some embodiments may be planar having a first planar surface and a second planar surface. Cryo-fracturing of amniotic membrane with a blunt object provides particles with less shear and a more irregular shape than conventional cryo-milling, thereby providing a higher surface area and more effective therapeutic effect.

The concentration of particles, such as micronized amniotic membrane, in the therapeutic composition may be provided in any effective amount such as more than about 0.1%, more than about 0.5%, more than about 1%, more than about 10%, more than about 25%, more than about 50%, more than about 75%, or more than about 90% by weight of therapeutic composition and any range between and including the weight percentages listed. Likewise, the mass of particles, such as amniotic membrane particles, may be provided in a therapeutic composition in any effective amount, such as more than about 0.1 mg/ml, more than about 1 mg/ml, more than about 5 mg/ml, more than about 10 mg/ml, more than about 50 mg/ml, more than about 100 mg/ml, more than about 500 mg/ml, and any range between and including the mass concentrations provided. The particles in the therapeutic composition may comprise collagen, growth factors, stem cells, amniotic stem cells, mesenchymal stem cells, progenitor cells, red blood cells, white blood cells, proteins, fibroblasts, paratenacytes, keratinocytes and the like.

Additional fluids and agents may be added to the acellular amnion derived therapeutic composition including, but not limited to, Plasma Lyte-A, from Baxter Inc., saline and the like. An acellular amnion derived therapeutic composition, as described herein, may comprise anti-inflammatory nanoparticles and/or statins, and HMG-CoA reductase inhibitors to reduce inflation at a treatment location.

An acellular amnion derived therapeutic composition may comprise proteins, growth factors and cytokines derived from the placental tissue, such as amniotic membrane or fluid. Amnion derived protein may be identified in an acellular amnion derived therapeutic composition by a protein marker including, but not limited to, basic fibroblast growth factors (bFGF), bone morphogenetic protein 2 (bmp-2), bone morphogenic protein 4 (bmp4), bone morphogenetic protein 7 (bmp-7), bone morphogenic protein 9 (bmp-9), epidermal growth factor (EGF), insulin-like growth factor 1 (IGF-1), platelet-derived growth factor AA (PDGF-AA), platelet growth factor BB (PDGF-BB), platelet growth factor AB (PDGF-AB), transforming growth factor beta one (TGF-b1), and vascular endothelial growth factor (VEGF). Flow cytometry may be used to identify proteins markers such as, CD44, CD105, CD73, CD90, CD29, CD166, CD58 and other proteins found in amnion material, it is to be understood that any number of protein markers common to amniotic material may be identified in a composition to determine if the composition is amnion derived. Any other material derived from amnion material including the membrane and fluid may be included in an acellular amnion derived therapeutic composition, as described herein.

An acellular amnion derived therapeutic composition may be decellularized, made acellular, through any suitable means including, but not limited to, sterilization, lyophilizing, freezing, centrifuging, radiation exposure, chemical treatment and the like. In some embodiments, a therapeutic composition is acellular through a process of destroying or making inactive any live cells, such as amniotic stem cells. In another embodiment, essentially all cells, including amniotic stem cells, are removed from the therapeutic composition through filtration and/or centrifugation wherein no more than about five percent, no more than about three percent, no more than about two percent, or no more than about one percent of an original quantity of intact cells remains in a therapeutic composition, as described herein. In yet another embodiment, a therapeutic composition is acellular, comprising a plurality of dead cells, such as amniotic stem cells. Dead and/or destroyed cells may release proteins and growth factors into the therapeutic composition. An acellular therapeutic composition may comprise particles of amniotic membrane, such a cyrofractured or morselized amniotic membrane, as described herein. In another embodiment, an acellular amnion derived therapeutic composition consists of a fluid component that is essentially free of cells. For example, amniotic fluid may be centrifuged to substantially remove all the amniotic cells, including dead cells. In one embodiment, an acellular amnion derived therapeutic composition is sterilized and then stored at ambient temperature, or refrigerated to a temperature of greater than 0° C., frozen at a temperature of between about 80° C. to about 0° C., or is cryogenically stored at a temperature of less than about −80° C., prior to use.

An acellular amnion derived therapeutic composition may be dehydrated to reduce the moisture content to below 5%, and preferable below 2% and even more preferably to below 1%. A therapeutic composition, as described herein, including the a therapeutic fluid, placental tissue particles, support layer, amniotic membrane and combinations thereof may be dehydrated through freeze drying, air drying, application of heat and/or vacuum and the like.

Any of the acellular amnion derived therapeutic compositions described herein may be an injectable solution that will pass through any suitable needle, including 16 to 30 gauge needles or larger diameter needle. In some applications an acellular amnion derived therapeutic composition is provided through micro or nano-needles. An acellular amnion derived therapeutic composition may be provided to a patient transcatheter. In other embodiments, an acellular amnion derived therapeutic composition is provided in a thicker composition, such as a paste that may be applied topically. The viscosity of the injectable acellular amnion derived therapeutic composition may be no more than about 1 mPa sec, no more than about 500 mPa sec, no more than about 1000 mPa sec, no more than 20,000 mPa sec, no more than 50,000 mPa sec and any range between and including the viscosity values provided.

In other embodiments, an acellular amnion derived therapeutic composition may be provided for topical applications and the viscosity may be more than about 20 Pa sec, more than about 50 Pa sec, more than about 100 Pa sec, more than about 250 Pa sec and any range between and including the viscosity values provided.

The acellular amnion derived therapeutic composition described herein may be cryopreserved, whereby the temperature of the therapeutic composition is lowered to a temperature of no more than −65° C., and preferably lower than about −80° C. The rate of cooling may be controlled to reduce damage and maintain viability of the cells upon thawing.

An acellular amnion derived therapeutic composition, as described herein, may comprise an amniotic membrane to create an acellular therapeutic composite. A therapeutic composite comprising an amniotic membrane may be used in any suitable treatment method of use, as described herein. An amniotic membrane may be provided in a multilayered configuration or combined with any other suitable matrix component for a desired application. For example, an acellular therapeutic composite, as described herein, may comprise an amniotic membrane layer and a cover layer. A cover layer may be used to reduce the loss or wash-out of a fluid component from the acellular therapeutic composite. In another embodiment, the acellular therapeutic composite comprises an amniotic membrane and a support layer, such as a polymer matrix material including, but not limited to, a bioresorbable or fluoropolymer membrane. A support layer may have a tensile break strength that is much greater, such as two times or more, than that of an amniotic membrane layer in a matrix component. In still another embodiment, an acellular amnion derived therapeutic composite comprises one or more layers of amniotic membrane that are tensilized, whereby an amniotic membrane has been stretched in one or more directions to increase strength and/or area of the membrane. An amniotic membrane may be cross-linked, and a cross-linked amniotic membrane may be combined with a non-cross-linked amniotic membrane. Any suitable method as known in the art of cross-linking an amniotic membrane may be used including, but limited to, chemical treatment with glutaraldehyde, radiation and the like.

In another embodiment, a fluid component of an acellular amnion derived composite comprises amniotic membrane that has been micronized and dispersed in a fluid. In one embodiment, a fluid component is a dispersion of micronized amniotic membrane combined with a fluid, such as plasma, saline, amniotic fluid, combinations thereof and the like. In an exemplary embodiment, the fluid component and amniotic membrane are from a single donor. A fluid component, as described herein, may comprise anti-inflammatory nano-particles anchor statins, or HMG-CoA reductase inhibitors to educe inflammation at a treatment location.

An acellular amnion derived therapeutic composite, as described herein, may be provided with the fluid component imbibed into, coated onto or otherwise applied to a matrix component. For example, an acellular amnion derived therapeutic composite comprising an amniotic membrane may be provided with a fluid component comprising micronized placental tissue particles dispersed in concentrated or diluted acellular amniotic fluid component. In an exemplary embodiment, the amniotic membrane and a fluid component are all from a single donor. In another exemplary embodiment, a therapeutic composite comprises an amniotic membrane layer configured for direct application to a treatment location, a cover layer of a bioresorbable material and a fluid component. A portion of a bioresorbable material or other matrix layer of the therapeutic composite may be porous to enable a portion of the fluid component to be retained therein. Any suitable number and type of matrix or support layers may be configured in a therapeutic composite, as described herein. In one embodiment, a fluid component may be vacuum imbibed into a matrix component, whereby a matrix component is submerged in a fluid component and vacuum is applied to remove air from the matrix component. This removal of air allows the fluid component to more substantially fill the voids and porosity of the matrix component.

A support layer may comprise any suitable type of material including, but not limited to a bioresorbable material, a non-bioresorbable polymer material, such a polyether ether ketone (PEEK), or polytetrafluoroethylene (PTFE), fluorinated ethylene propylene (FEP), perfluoroalkoxy (PFA) and the like, or a metallic component, such as stainless steel, titanium, gold and the like. A support layer may be porous and/or permeable. A support layer may be a membrane having a microstructure of pores, or a film, net, screen, woven and the like. A support layer may be substantially non-permeable to fluid and may be hydrophobic or oleophobic on at least one side. In an exemplary embodiment, a support layer is expanded PTFE. In an exemplary embodiment, a support layer is a sheet of material having a first substantially planar surface, a second substantially planar surface and a thickness. An acellular amnion derived composition, may be provided with a stent, such as a self-expanding stent comprising Nitinol or a covered stent having a stent cover over at least a portion of the stent, such as an expanded fluoropolymer material. An acellular amnion derived composition may be coated directly onto a self-expanding stent, or an acellular amnion derived composition may be coupled to the stent. For example, an acellular amnion derived composition comprising an amnion membrane support layer may be attached to a self-expanding stent. Expanded PTFE is often used in covered stent applications and an acellular amnion derived composition may be coated onto or imbibed into the porosity, or pores of an expanded PTFE material.

Any of the acellular amnion derived therapeutic composition described herein may be used for a wide variety of treatment applications including, but not limited to, any organ, respiratory system, circulatory system, digestive system, central nervous system and the like. A therapeutic composition, as described herein, may be provided to any suitable treatment location of the body to induce an immunomodulatory and/or anti-inflammatory response. In another application, a therapeutic composition is introduced into a treatment location to reduce scaring and to promote healing, whereby the therapeutic composition aids in regeneration of new tissue. A therapeutic composition may be injected directly into an affected area or introduced intravenously.

An effective dose of an acellular therapeutic composition may be provided in one treatment or in several doses over a period of time. The specific treatment and dosing regime will depend on the type and severity of the condition to be treated.

In one embodiment, an acellular amnion derived therapeutic composition is injected into a specific treatment location through the use of a catheter, such as a steerable catheter and an injection implement configured on the introductory end of the catheter. For example, a catheter having an injection implement may be introduced to an artery, inserted to position the injection implement in proximity of the treatment location, whereby a dose of therapeutic composition is administered into the treatment location.

An acellular amnion derived therapeutic composition, as described herein, may be used in conjunction with any suitable matrix component including bioresorbable materials, synthetic polymer material, bone (cortical or cancellous) and membranes and the like. The therapeutic composition may be imbibed into, coated onto or otherwise combined with a matrix component for treatment. In an exemplary embodiment, a therapeutic composition is coated into a porous bioresorbable material and placed onto a treatment location.

An acellular amnion derived therapeutic composition may be a cosmetic composition and comprise one or more cosmetic components, as defined herein. An acellular amnion derived therapeutic composition may be a cosmetic composition that is configured for topical application (i.e. hydrogel, transdermal membrane, reservoir, microneedle type array) to the skin of a subject to reduce wrinkles, discolorations, improve appearance and the like. Cosmetic composition, as used herein, is defined as any substance or preparation intended to be placed in contact with the various external parts of the human body for the purpose to clean, perfume, change the appearance, protect, keep in good condition, or correct body odors. A cosmetic composition may comprise any suitable combination of cosmetic components including, but not limited to, water, hyaluronic acid, alcohols such as polyhydric, ethylene glycol, propylene glycol, trimethylene glycol, butylene glycol, isoprene glycol and sorbitol, hydrocarbon polymers, silicone polymers, silicone emollient, silicone oligomer, natural oils derived from plants or animals, such as fruit or vegetable derived oils, mineral oil, wax, borax, acids including polylactic acids and surfactants.

An acellular amnion derived therapeutic composition may be made from amnion tissue and/or fluid from any suitable mammalian donor, including humans, horses, pigs, and the like. In addition, an acellular amnion derived therapeutic composition may be used to treat a treatment location of any suitable mammalian patient, including a human or horse for example.

The summary of the invention is provided as a general introduction to some of the embodiments of the invention, and is not intended to be limiting. Additional example embodiments including variations and alternative configurations of the invention are provided herein.

Any suitable therapeutic composition as described herein, and particularly a therapeutic composition comprising, acellular amniotic membrane particles and a carrier fluid comprising an acellular amniotic fluid; wherein the acellular amniotic membrane particles consist essentially of micronized amniotic membrane and wherein the therapeutic composition is essentially free of any viable amniotic membrane cells or viable amniotic fluid cells, may be used to treat a wide variety of treatment locations. A therapeutic composition may be applied topically to an external body treatment location or internally during an intraoperative procedure, and may be in the form or a cream, gel, lotion, or ointment, and/or may be configured into a patch or other delivery article. A therapeutic composition may be injected into a treatment location, through the use of a syringe with or without needles or in some cases a syringe coupled with a catheter into the arterial, venous, cerebrospinal systems. A therapeutic composition may be introduced intravenously, including transcatheter, intra-arterial or through cerebrospinal treating. A therapeutic composition may be introduced to a treatment location during an intraoperative procedure and the therapeutic composition may be applied topically, within a patch or other delivery article, or injected into a treatment location, for example. A therapeutic composition may be administered orally and may be in the form of a liquid, a capsule, or tablet.

A therapeutic composition, as described herein, may be applied topically to a treatment location, such as an external body treatment location. An external body treatment location is any portion or location of the body that can be treated through direct application of the therapeutic composition without any invasive measures, such as invasive surgery or the use of instruments, such as scopes or catheters. External body treatment locations include, but are not limited to, skin, hair or scalp, eyes, nose and mucous membranes, mouth and the oral cavity including the teeth and gums, and the ears. Topical treatment may involve direct application of the therapeutic composition to a treatment location or may involve spraying the therapeutic composition onto a treatment location, such as the mucous membranes in the nose or mouth or into or on vaginal tissue. In addition, the therapeutic composition may be in the form of a liquid, cream, gel, lotion or ointment. A cream is a semisolid dosage form containing one or more therapeutic compositions dissolved or dispersed in a suitable base. A gel is a semisolid system consisting of either suspensions made up of small inorganic particles or large organic molecules interpenetrated by a liquid. A lotion is used to categorize a topical suspensions, solutions and emulsions intended for application to the skin. An ointment is a semisolid preparation intended for external application to the skin or mucous membranes. In addition, a therapeutic composition, in any of the forms described herein, may be coupled with a delivery article, such as a patch or covering. For example, a therapeutic composition may be imbibed into a porous material that is configured as a patch or wound covering. A wound includes, but is not limited to, a break or cut in the skin or tissue, chronic wounds, diabetic wounds, venous leg ulcers, acute wounds, traumatic wounds, gangrene, surgical wounds, pressure ulcers, arterial ulcers, and neuropathic wounds.

An external body treatment location includes, skin, hair, hair follicle, or surrounding tissue, wound, i.e. a cut or break in the skin, cut, abrasion, ulcer, boil, ophthalmic lesion, pimple, a first, second or third degree burn, scar, keloid scar, eye, mouth, nose, mucous membrane and the like. A therapeutic composition may be used to treat a wide range of dermatological disorders, diseases, or conditions including, but not limited to, lupus, acne, blisters, psoriasis, rosacea, eczema, keloid, scars, shingles, skin aging, dry skin, wrinkles, alopecia, Steven-Johnson syndrome, and skin cancer. A therapeutic composition may be used to increase the rate of healing of an external body treatment location, such as a cut, wound, or abrasion. A therapeutic composition may be used to treat hair loss local or systemic i.e. alopecia, hair loss immunmodulated or chemically induced or hormonally induced. A therapeutic composition may be used to treat atopic dermatitis of any etiology including immunmodulated i.e. psoriasis, vitiligo or allergic response eczema (dyshidrotic), atopic from external irritant.

A therapeutic composition, as described herein, may be injected into a treatment location. A therapeutic composition may be configured into a syringe, for example, and the needle of the syringe may be inserted into treatment location for injection of the therapeutic composition, therein. A needle may pass into or through an external body portion, such as the skin, to inject the therapeutic composition internally or into an internal body portion, such as a muscle. In addition, during an intraoperative procedure, a therapeutic composition may be injected directly into an internal body portion, such as an organ.

A therapeutic composition may be injected into any portion of a joint, such as an articular joint including, but not limited to, a muscle in or around the joint, a ligament, a tendon, a meniscus, a bone within or proximal to the joint and the like.

A therapeutic composition may be injected into a treatment location associated with the musculoskeletal system, digestive system, respiratory system, urinary system, reproductive system, endocrine system, circulatory system, nervous system and the integumentary system. Areas for injection associated with the musculoskeletal system include, but are not limited to, joints, muscles, tendons, bones, and the like. Areas for injection associated with the digestive system include, but are not limited to, mouth, teeth, tongue, salivary gland, parotid gland, submandibular gland, sublingual gland, pharynx, esophagus, stomach, small intestine, duodenum, jejunum, Ileum, large intestine, liver, gallbladder, pancreas and the like. Areas for injection associated with the respiratory system include, but are not limited to, nasal cavity, pharynx, larynx, trachea, bronchi, lungs, diaphragm and the like. Areas for injection associated with the urinary system include, but are not limited to, kidneys, ureters, bladder, urethra and the like. Areas for injection associated with the reproductive system include, but are not limited to, ovaries, fallopian tubes, uterus, vagina, vulva, clitoris, placenta, testes, epididymis, vas deferens, seminal vesicle, prostate, bulbourethral glands, penis, scrotum and the like. Areas for injection associated with the endocrine system include, but are not limited to, pituitary gland, pineal gland, thyroid gland, parathyroid gland, adrenal gland, pancreas and the like. Areas for injection associated with the circulatory system include, but are not limited to, heart or any portion thereof, arteries, veins, capillaries, and the like. Areas for injection associated with the lymphatic system include, but are not limited to, lymphatic vessel, lymph node, bone marrow, thymus, spleen and the like. Areas for injection associated with the nervous system include, but are not limited to, brain or any portion thereof, cerebral hemispheres, diencephalon, the brainstem, midbrain, pons, medulla oblongata, cerebellum, spinal cord, ventricular system, choroid plexus, peripheral nervous system, nerves, cranial nerves, spinal nerves, sensory organs including the eye or any portion thereof, cornea, iris, ciliary body, lens, retina, ear or any portion thereof, outer ear, earlobe, eardrum, middle ear, ossicles, inner ear, cochlea, vestibule of the ear, semicircular canals, olfactory epthelium, tongue, taste buds, and the like. Areas for injection associated with the integumentary system include, but are not limited to, skin, subcutaneous tissue, mammary glands and the like.

A therapeutic composition may be injected into a treatment location to increase the rate of healing or to treat a disorder or disease. For example, a therapeutic composition may be injected into an incision to promote the rate of healing of the wound caused by the incision. In another example, a therapeutic composition may be injected into or around the base of the penis for the treatment of erectile dysfunction or peyronie's disease. In still another example, a therapeutic composition in injected into or around the spine to treat a degenerative disease or condition of the intervertebral disc, facets, or vertebral end plates, for example. In yet another embodiment, a therapeutic composition is injected into a bone to treat osteoportic, traumatized with fracture bruising, non healing fracture, surgical repair of bone, to enhance the rate of bone healing, in still another example, a therapeutic composition is injected into or around the bladder to treat cystitis, urinary incontinence, overactive bladder, interstitial cystitis, and/or bladder cancer. In still another example, a therapeutic composition in injected into or around the liver to treat cirrhosis. In still another example, a therapeutic composition in injected into or around the brain to treat, seizures, trauma, Parkinson, autism, Alzheimer.

A therapeutic composition, as described herein, may be introduced intravenously, including into a patient's venous, arterial, cardiac or cerebrospinal system Administering a therapeutic composition intravenously may be used to treat systemic conditions including, but not limited to, Neurologic origin: neuromuscular i.e. lou gehrig's disease, ALS, multiple sclerosis, Parkinsons, Dementia, Alzhiemers and the like. In addition, administering a therapeutic composition intravenously may be used to treat immunomodulated or autoimmune conditions, including, but not limited to, lupus erythematosus, sero (+) (−) arthritis, ulcerative colitis, chronic fatigue syndrome, Fibromyalgia. Administering a therapeutic composition intravenously may be used to treat cardiac related conditions including, but not limited to, myocardial infarction, atrial fibrillation, congestive heart failure, endocarditis, cardiomyopathy and the like. Administering a therapeutic composition intravenously may be used to treat urologic disorders or disease such as interstitial cystitis, erectile dysfunction, urinary incontinence, urinary tract infection, renal failure. Administering a therapeutic composition intravenously may be used to treat kidney disorder or disease including, but not limited to, chronic kidney disease based on measured or estimated GFR (Glomerular Filtration Rate). Administering a therapeutic composition intravenously may be used to treat pulmonary disorder or disease including, but not limited to asthma, chronic obstructive pulmonary disease (COPD), idiophathic pulmonary fibrosis, alveolitis, chronic parenchymal lung disease, pleural lung disease, trans-bronchial parenchymal disease or post-operative lung recovery and scaring. Administering a therapeutic composition intravenously may be used to treat disorders or, disease of the bladder, liver, heart, lungs, brain blood, neuromuscular and the like. A therapeutic composition, as described herein, may be introduced intravenously through introduction into the pulmonary artery, a central venous catheter, a trans-bronchial catheter, and the like.

A therapeutic composition, as described herein, may be introduced intraoperatively, wherein the therapeutic composition in administered to internal body treatment location during an intraoperative procedure. For example, during an operation, a patient's internal organs may be exposed through an incision and a therapeutic composition may be applied to an organ topically, or through direct injection into the organ. The needle of the syringe may be inserted directly into any internal body treatment location including an incision, an organ, or intestine, and the like. In another embodiment, a therapeutic composition is applied topically to an internal body treatment location or configured in a patch or delivery article and applied directly to an internal body treatment location.

A therapeutic composition, as described herein, may be administered orally and may be in the form of a liquid or gel, capsule or tablet. A patient may be directed to take an effective amount of therapeutic composition orally to treat a gastrointestinal disorder or disease, a stomach disorder or disease, a stomach ulcer, crohn's disease, gastrointestinal polyps and the like.

A therapeutic composition, as described herein, may be configured as a suppository and administered anally to treat, hemorrhoids and the like. A therapeutic composition may be applied topically or through injection to treat hemorrhoids as well.

A therapeutic composition, as described herein, may be administered in any effective way described herein to treat neuromuscular disease or disorders including, but not limited to, multiple sclerosis, myasthenia gravis, amyotropic lateral sclerosis, spinal muscular atrophy and muscular dystrophy.

A therapeutic composition, as described herein, may be administered in any effective way described herein to treat heart disease or disorders including, but not limited to, coronary artery disease, abnormal heart rhythms, congenital heart disease, cardiomyopathies, pericarditis and arterial fibrillation.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1A:
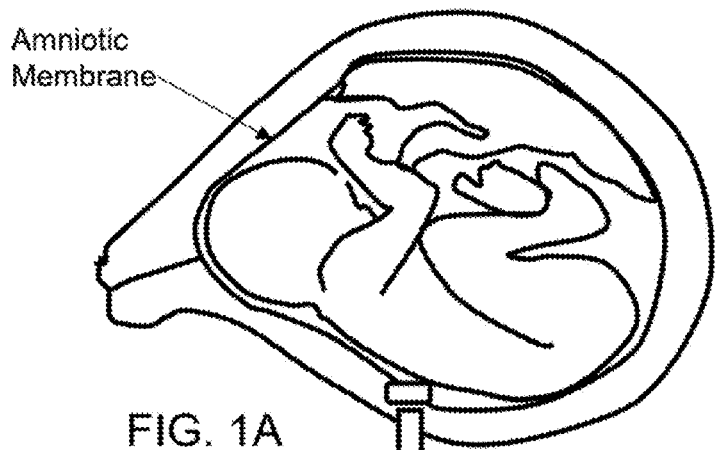

FIG. 1A shows a cross-sectional diagram of amniotic membrane surrounding a fetus in utero.

Figure 1B:
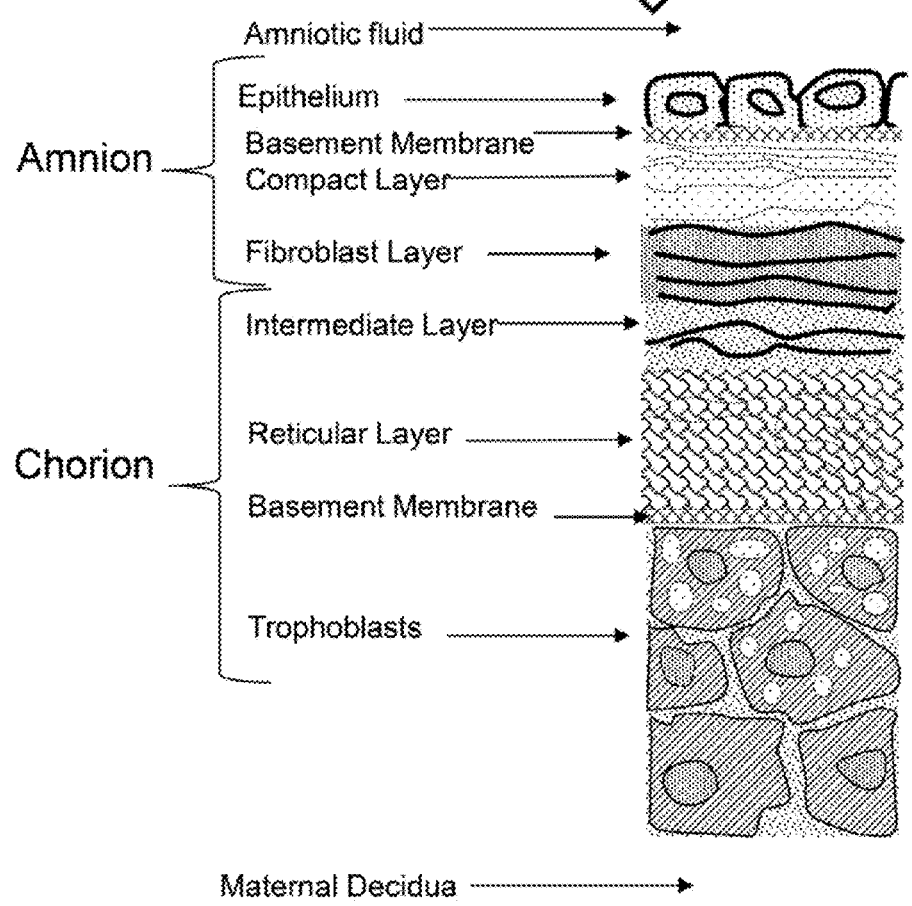

FIG. 1B shows a cross-sectional diagram of the layers of the amnion and chorion.

Figure 2A:
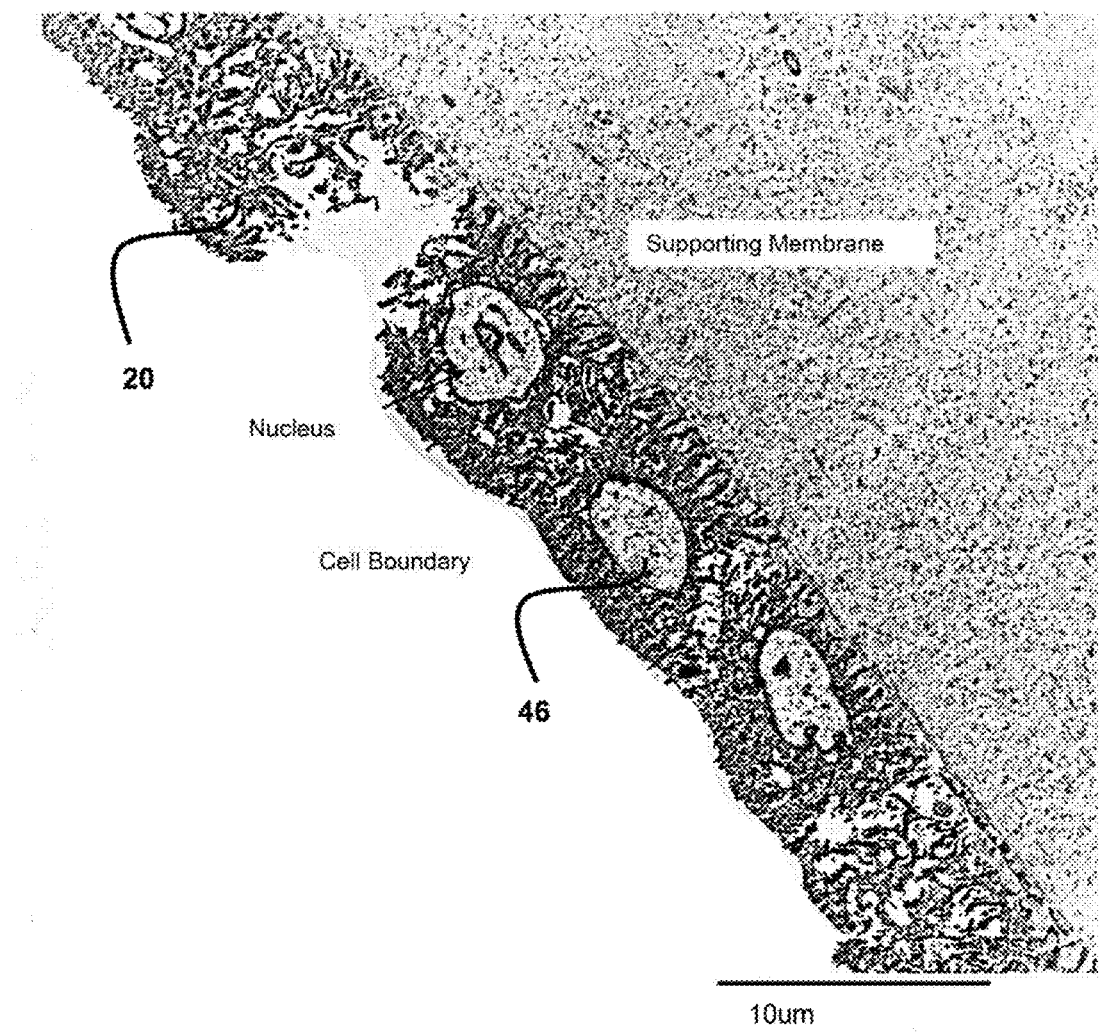

FIG. 2A shows a transmission electron micrograph (TEM) of the epithelium layer of the amniotic membrane having a single layer of amniotic cells. The TEM was taken at 2500× magnification.

Figure 2B:
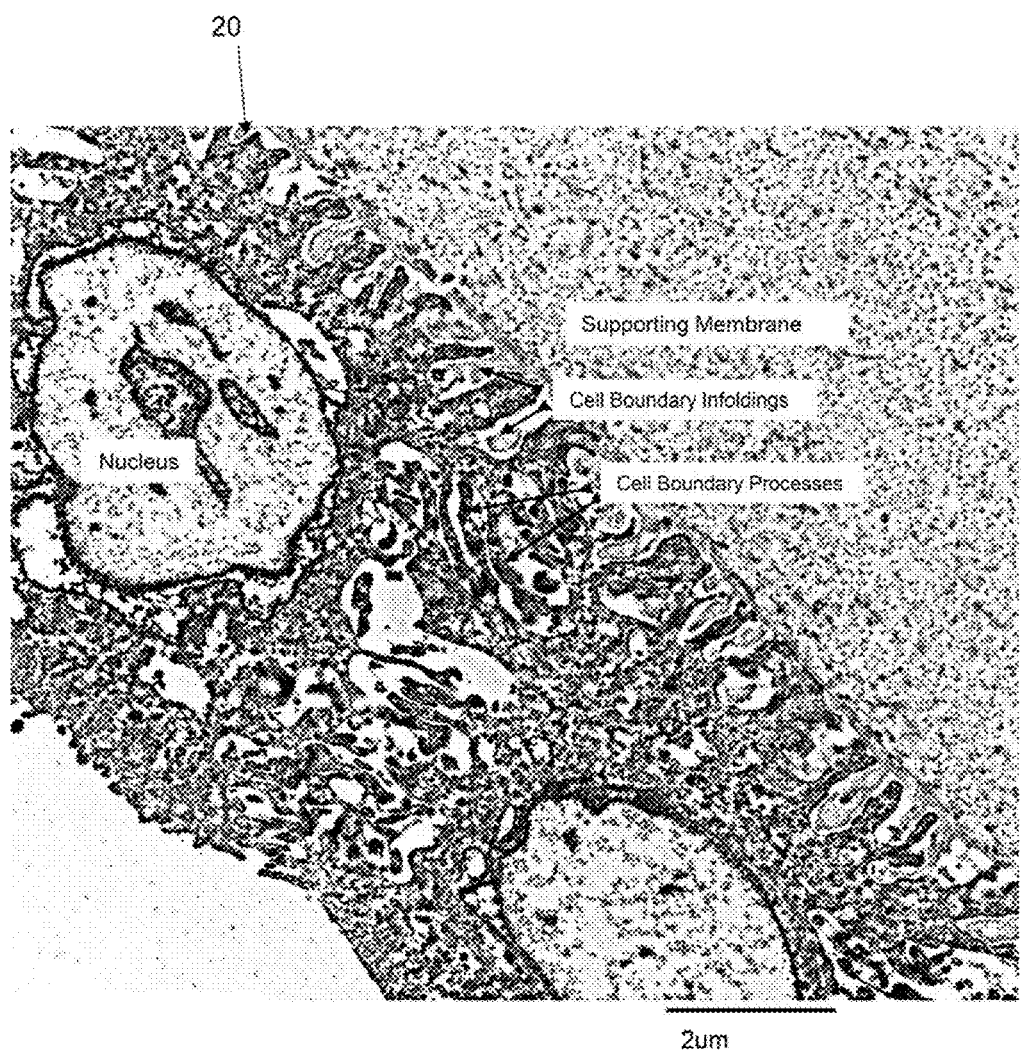

FIG. 2B shows a TEM of the epithelium layer of the amniotic membrane having a single layer of amniotic cells. The TEM was taken at 8200× magnification.

Figure 3A:
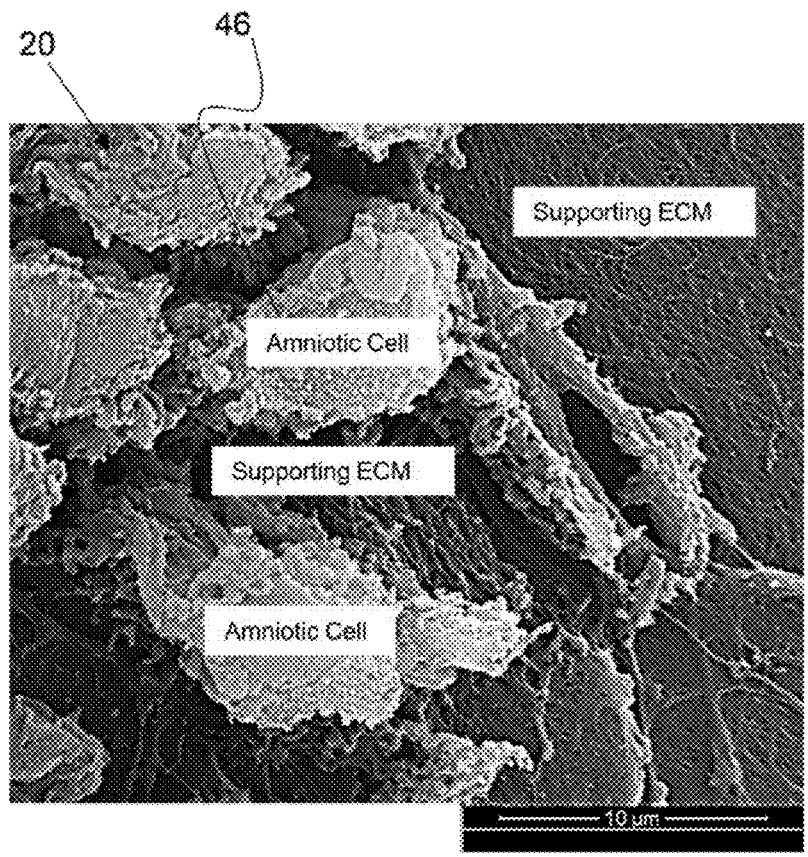

FIG. 3A is a scanning electron micrograph (SEM) of an amniotic membrane having amniotic cells.

Figure 3B:
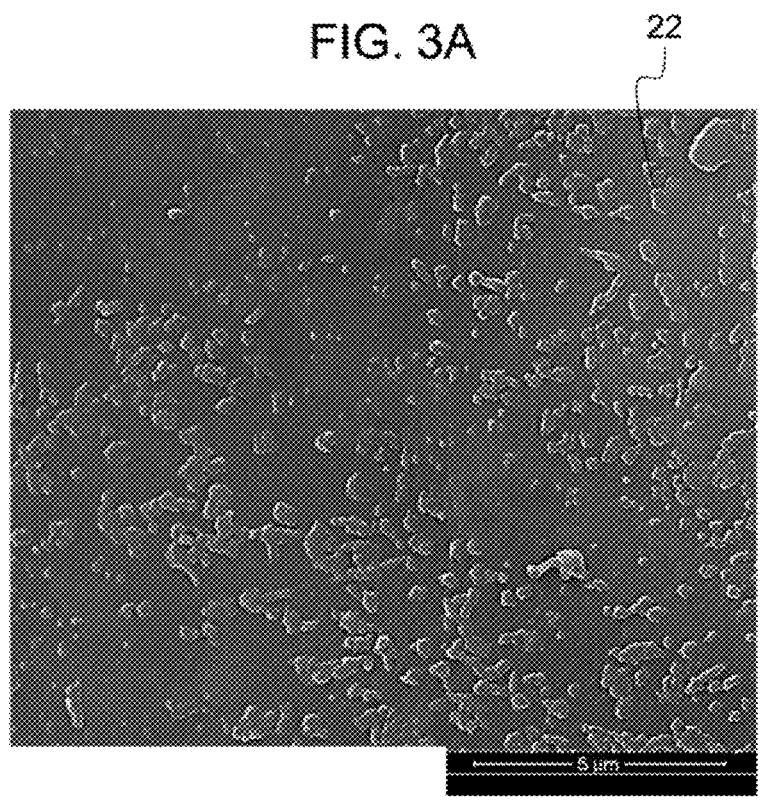

FIG. 3B is a SEM of cryo-fractured amniotic membrane particles.

Figure 4:
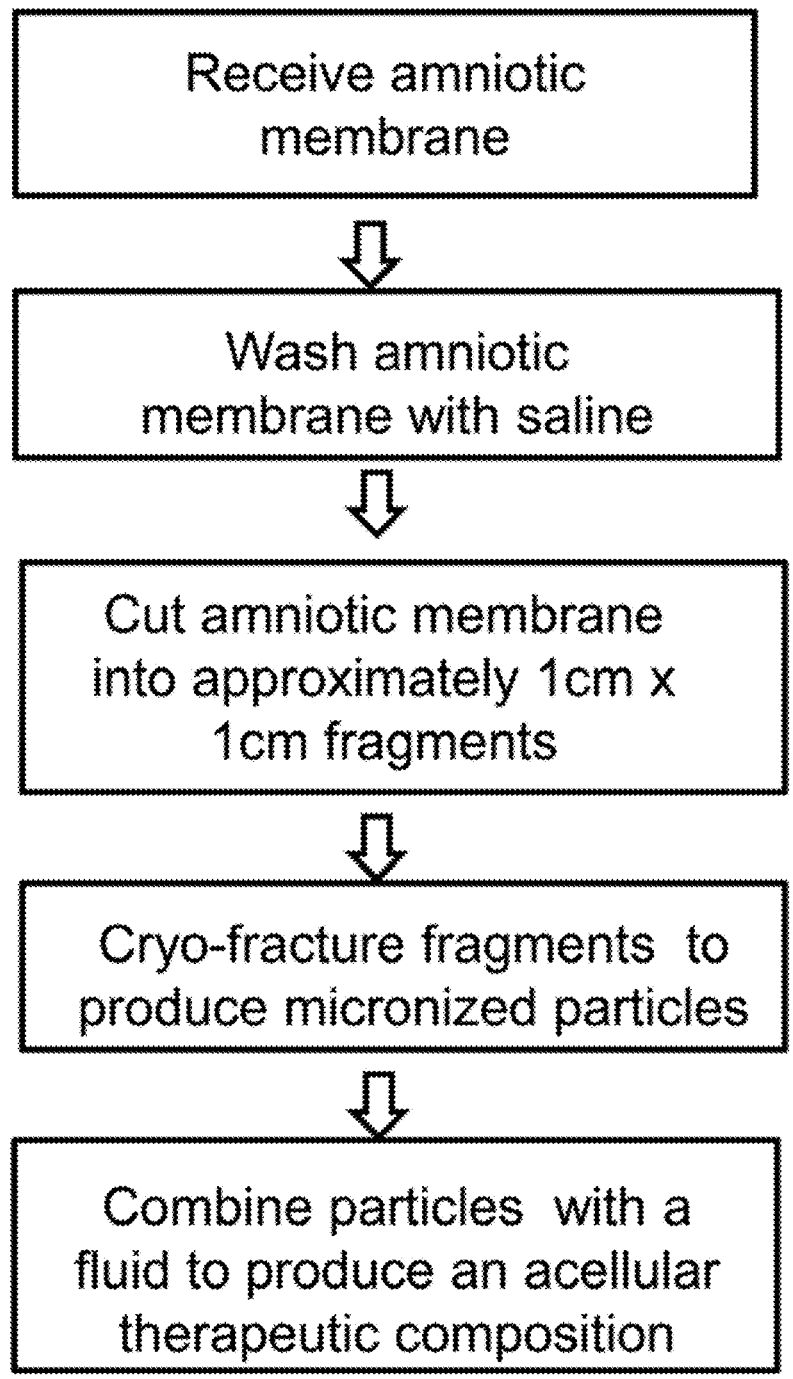

FIG. 4 shows a diagram of a process to produce an acellular amnion derived therapeutic composition comprising micronized amniotic membrane particles.

Figure 5:
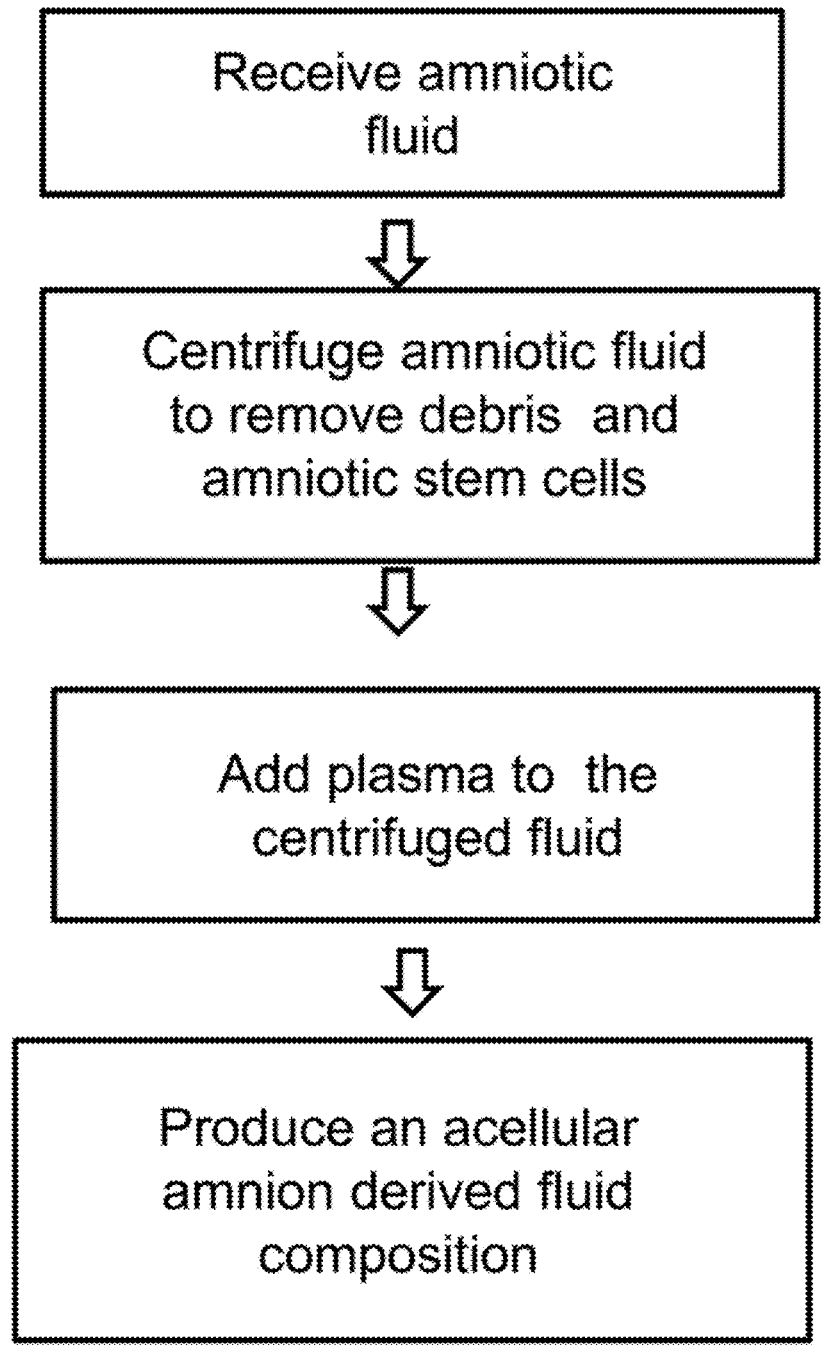

FIG. 5 shows a diagram of a process to produce an acellular amnion derived therapeutic composition comprising a concentrated amniotic fluid.

Figure 6:
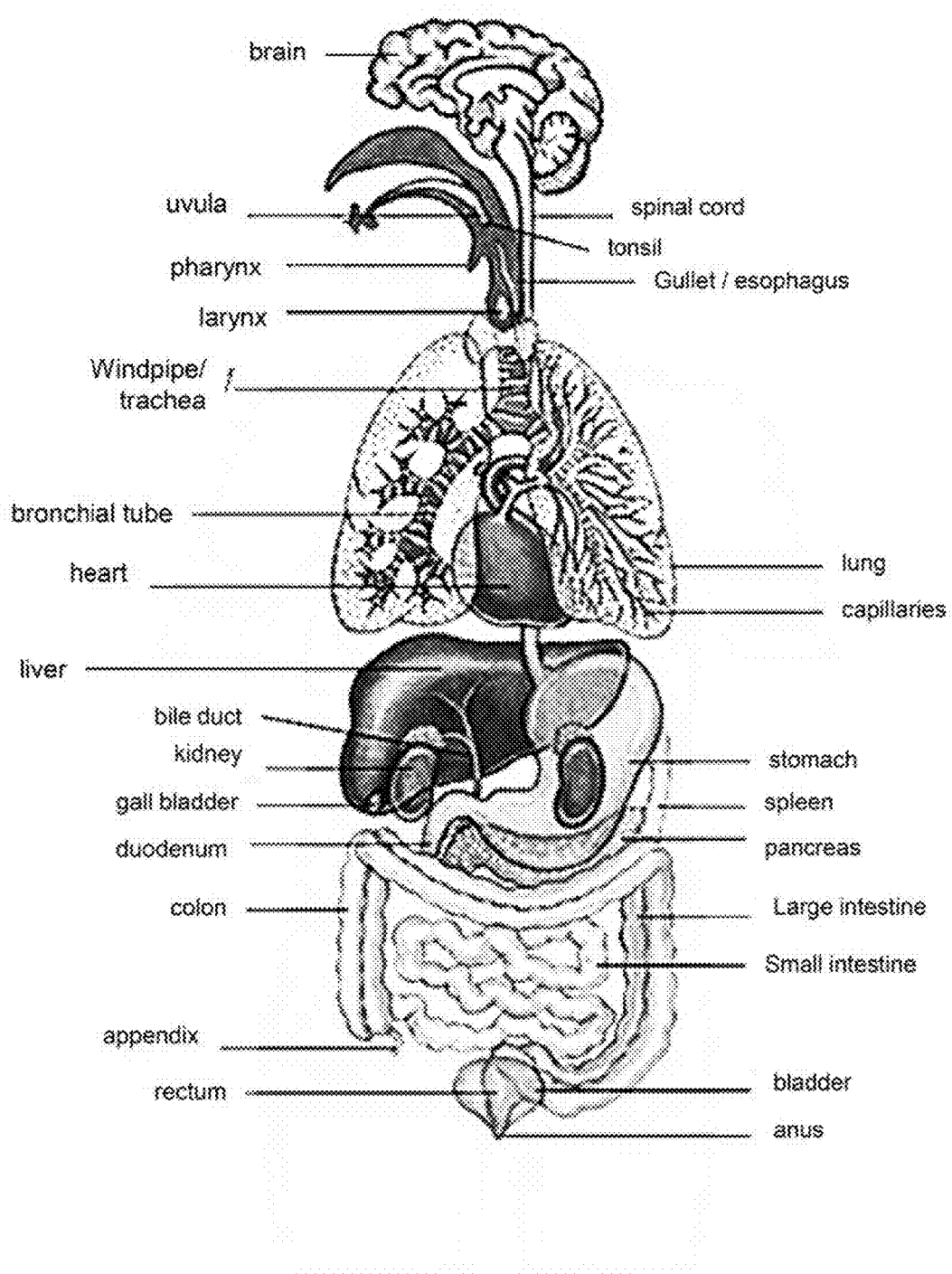

FIG. 6 shows a diagram of the anatomy and various organs within the body.

Figure 7:
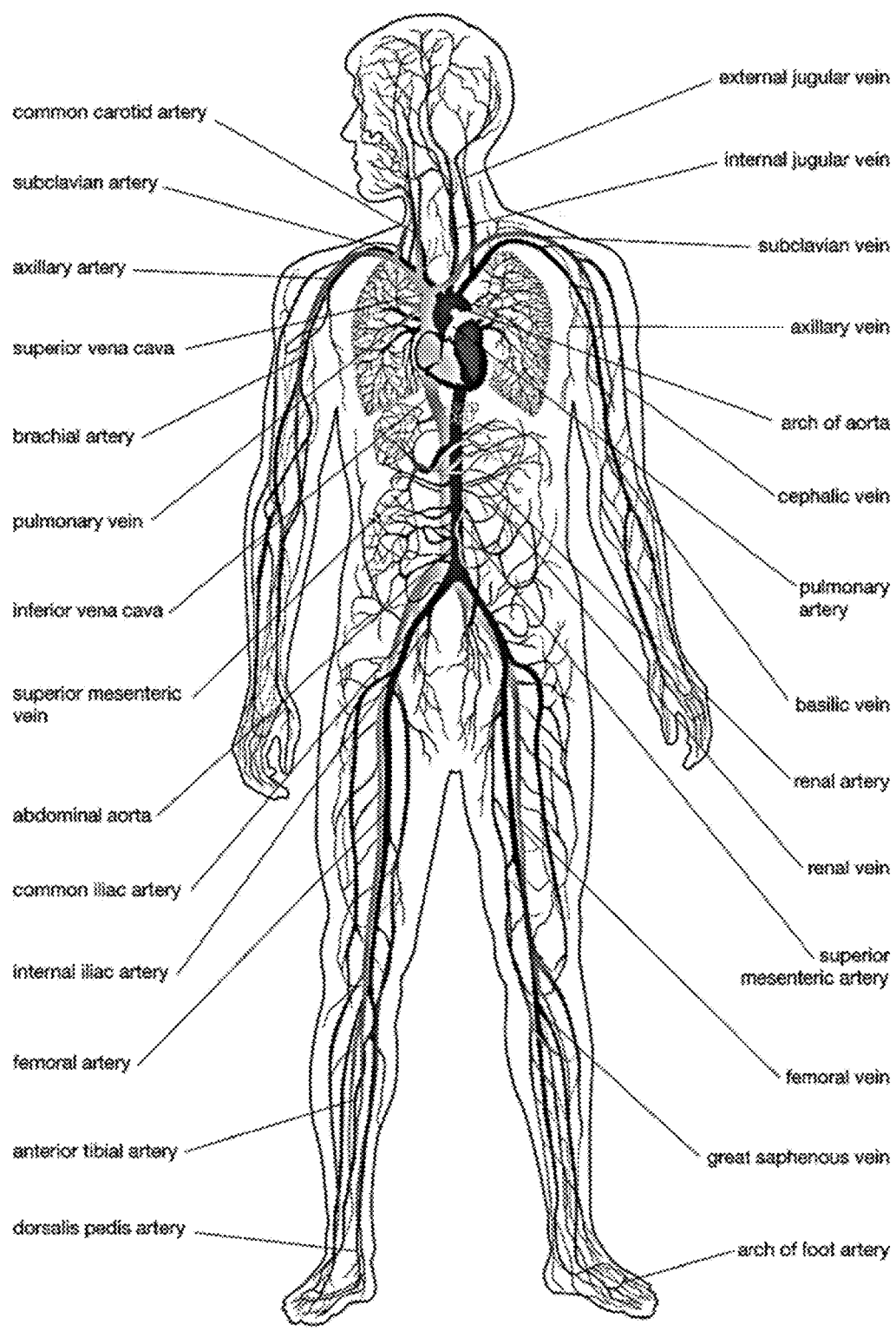

FIG. 7 shows a diagram of the circulatory system.

Figure 8:
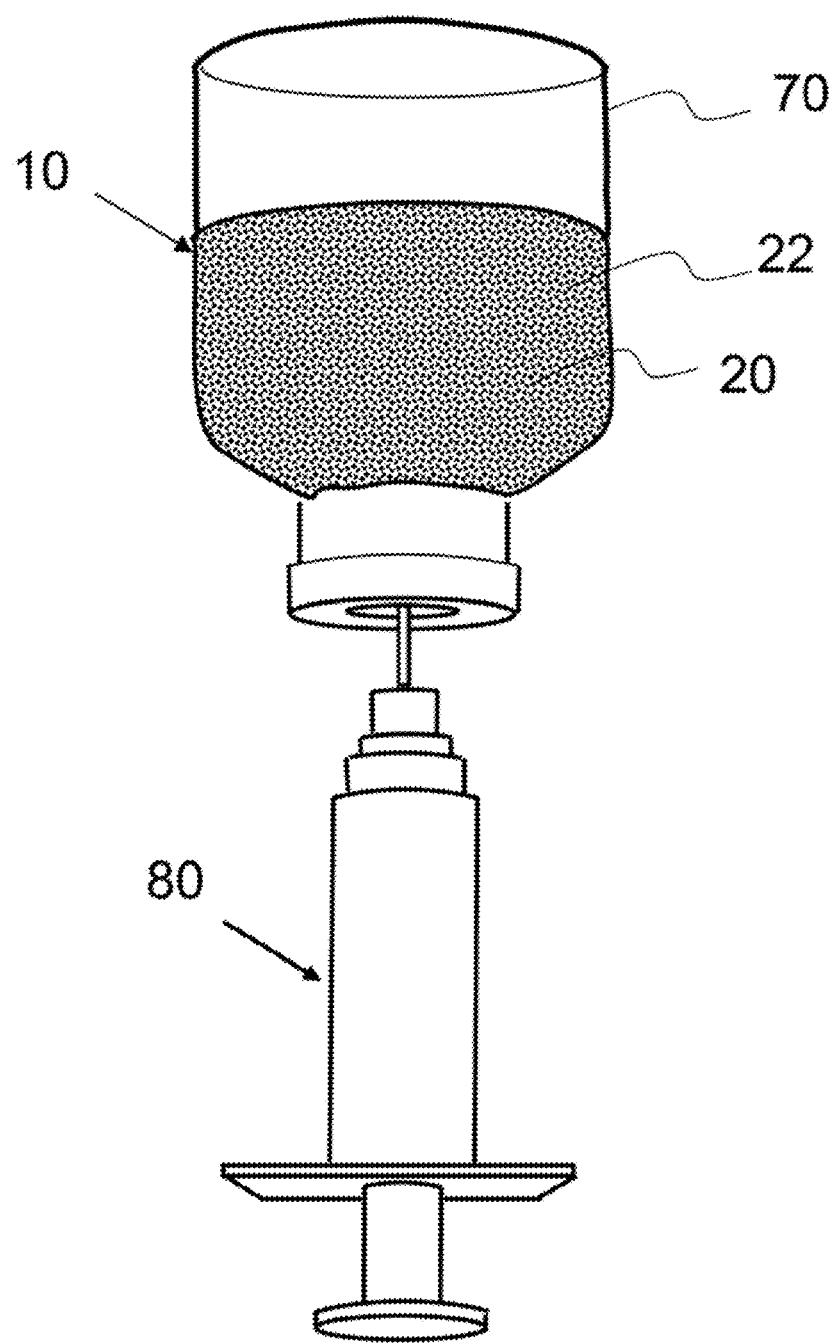

FIG. 8 shows an exemplary acellular amnion derived therapeutic composition being drawn from an enclosure by a needle.

Figure 9:
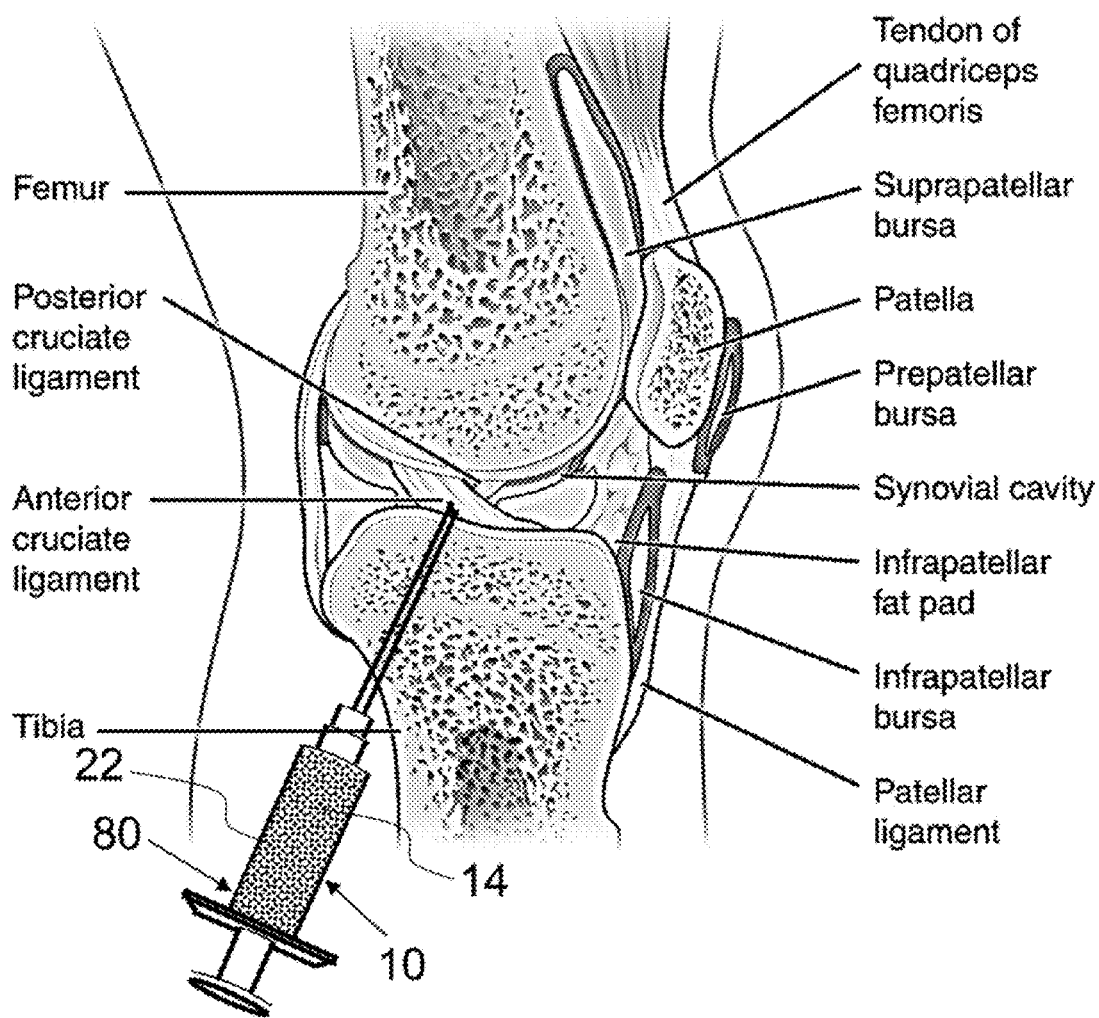

FIG. 9 shows a knee joint and a syringe injecting acellular amnion derived therapeutic composition into the knee joint.

Figure 10:
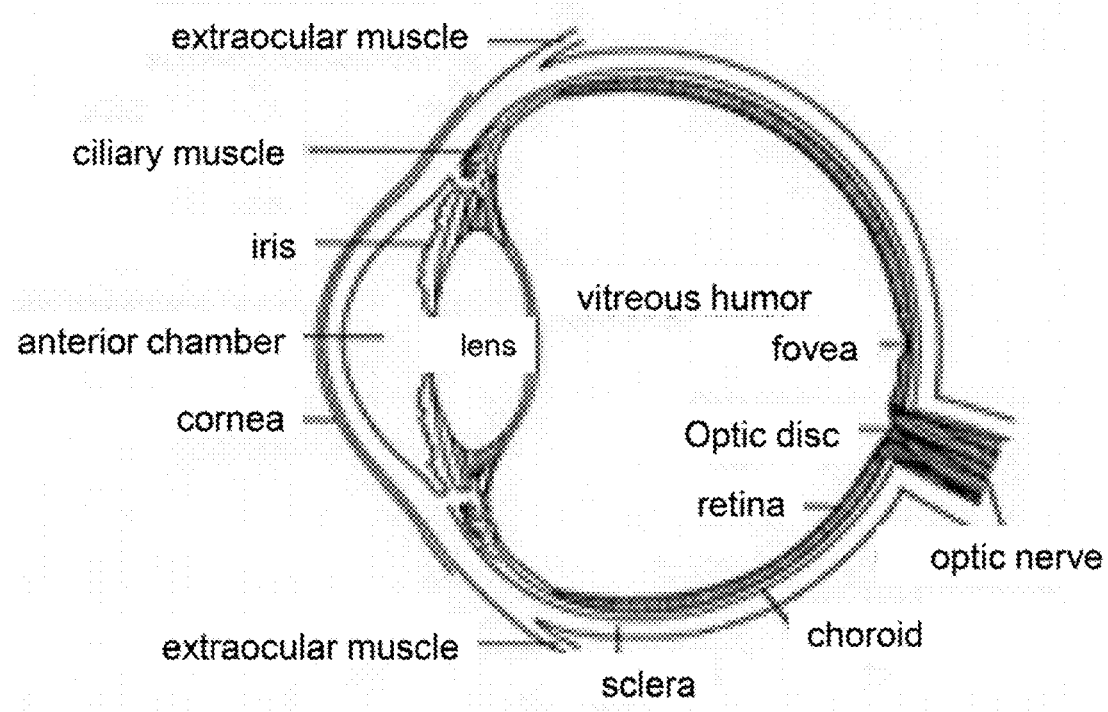

FIG. 10 shows a cross-sectional diagram of an eye.

Figure 11:
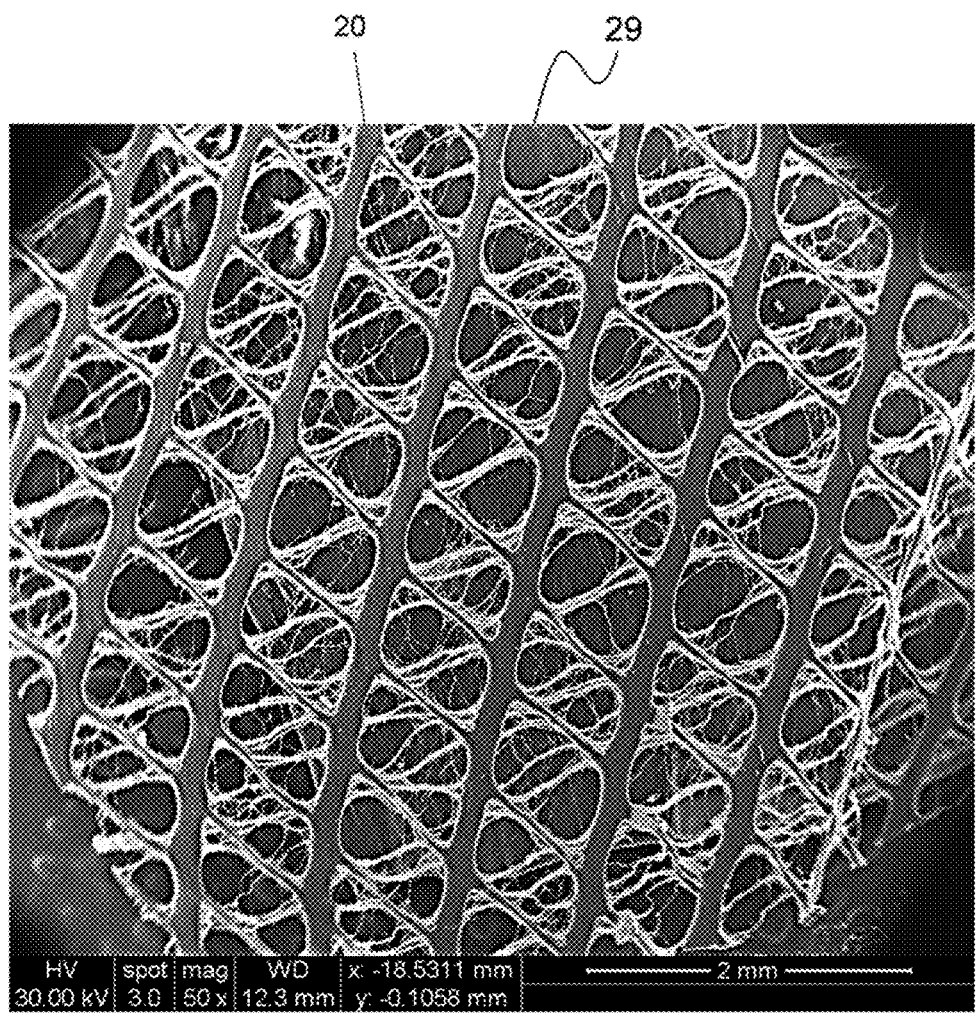

FIG. 11 is a scanning electron micrograph (SEM) representation of amniotic membrane having pores between the amniotic membrane tissue.

Figure 12A:
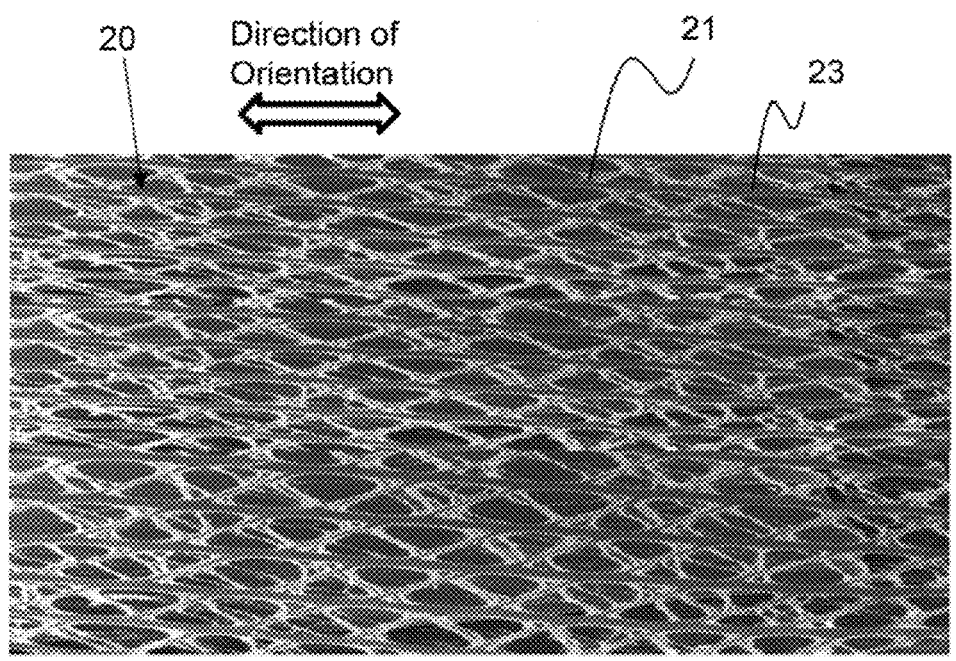

FIG. 12A is a representation of an exemplary tensilized amniotic membrane.

Figure 12B:
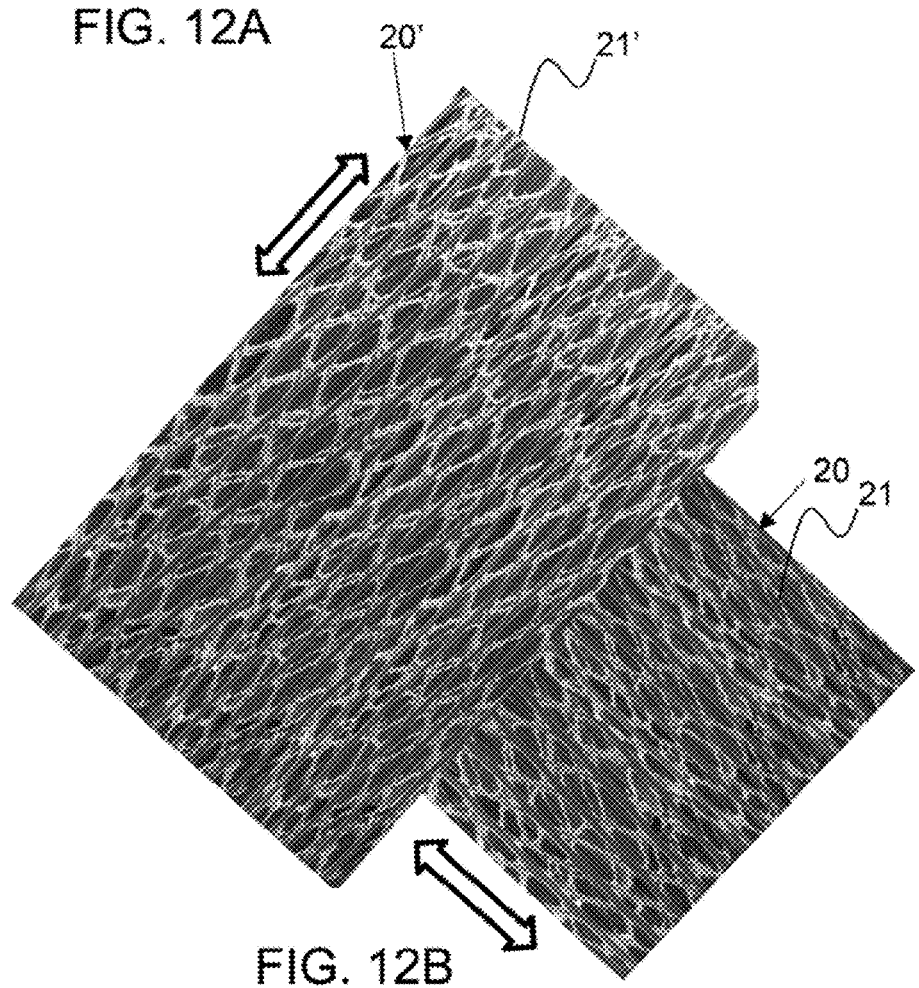

FIG. 12B is a representation of two exemplary tensilized amniotic membranes being layered together.

Figure 13:
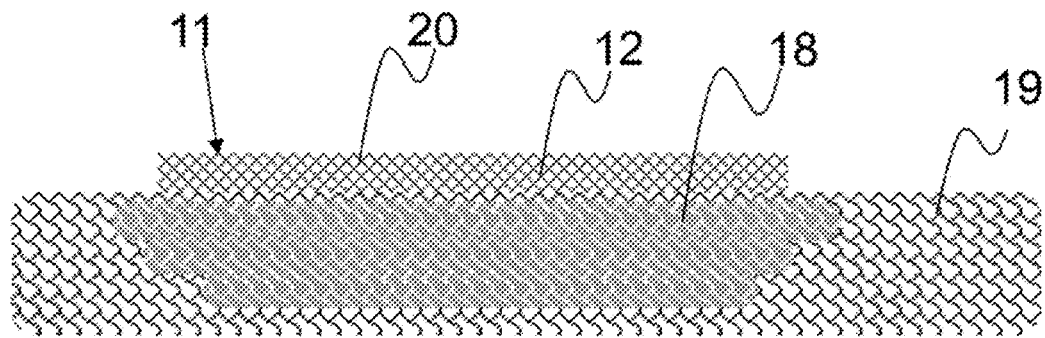

FIG. 13 shows a cross-sectional representation of an exemplary acellular amnion derived therapeutic composite comprising an amniotic membrane configured over a treatment location.

Figure 14:
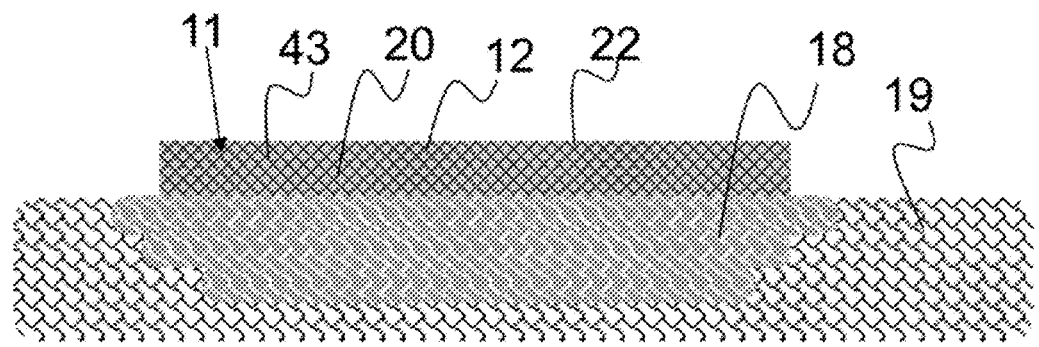

FIG. 14 shows a sectional representation of an exemplary acellular amnion derived therapeutic composite comprising an amniotic membrane and fluid component configured over a treatment location.

Figure 15:
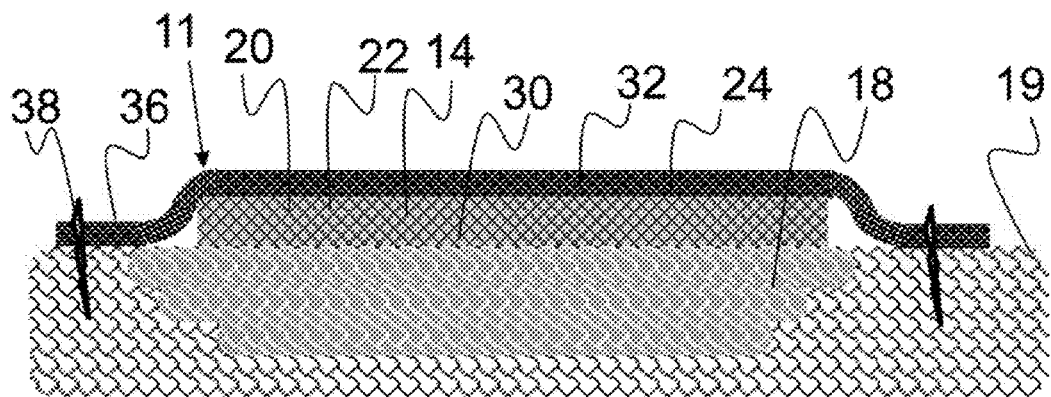

FIG. 15 shows a cross-sectional representation of an exemplary acellular amnion derived therapeutic composite configured over a treatment location wherein the therapeutic composite comprises an amniotic membrane imbibed with a fluid component and a cover layer configured there over.

Figure 16:
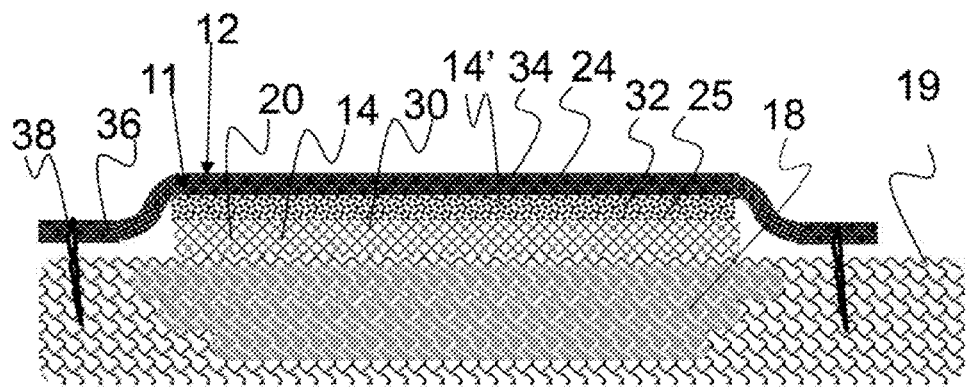

FIG. 16 shows a cross-sectional representation of an exemplary acellular amnion derived therapeutic composite configured over a treatment location wherein the therapeutic composite comprises a first matrix layer of amniotic membrane, a second matrix layer of a fluid component reservoir, and a third matrix layer that is a cover layer.

Figure 17:
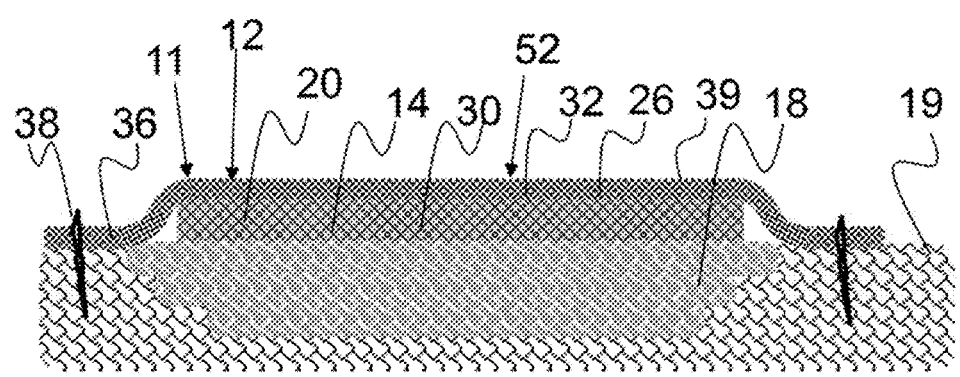

FIG. 17 shows a cross-sectional representation of an exemplary acellular amnion derived therapeutic composite configured over a treatment location wherein the therapeutic composite comprises a first matrix layer of amniotic membrane imbibed with fluid component and a second matrix layer that is a support layer comprising bioresorbable material.

Figure 18:
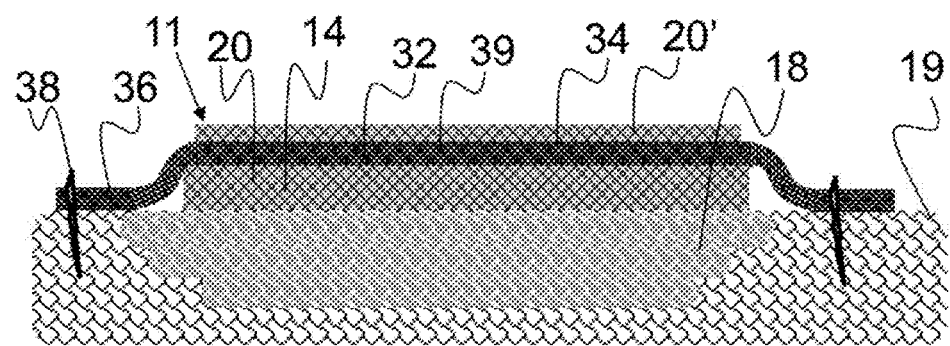

FIG. 18 shows a cross-sectional representation of an exemplary acellular amnion derived therapeutic composite configured over a treatment location wherein the therapeutic composite comprises a first matrix layer of amniotic membrane imbibed with fluid component, a second matrix layer that is a support layer and a third matrix layer that comprises amniotic membrane.

Figure 19:
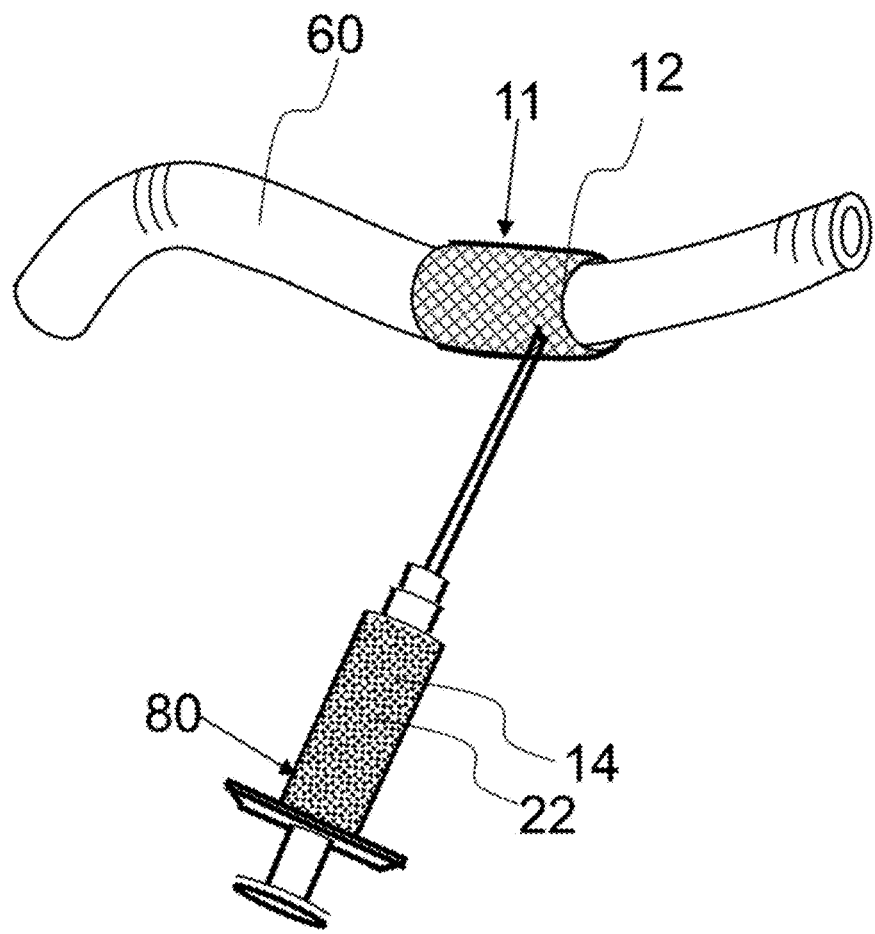

FIG. 19 shows an exemplary therapeutic composite configured around a ureter and a fluid component being injected therein.

Figure 20:

FIG. 20 shows a picture of a wound on a diabetic person's foot prior to treatment.

Figure 21:

FIG. 21 shows an x-ray of an osteochondral defect in an ankle, prior to treatment.

Figure 22:
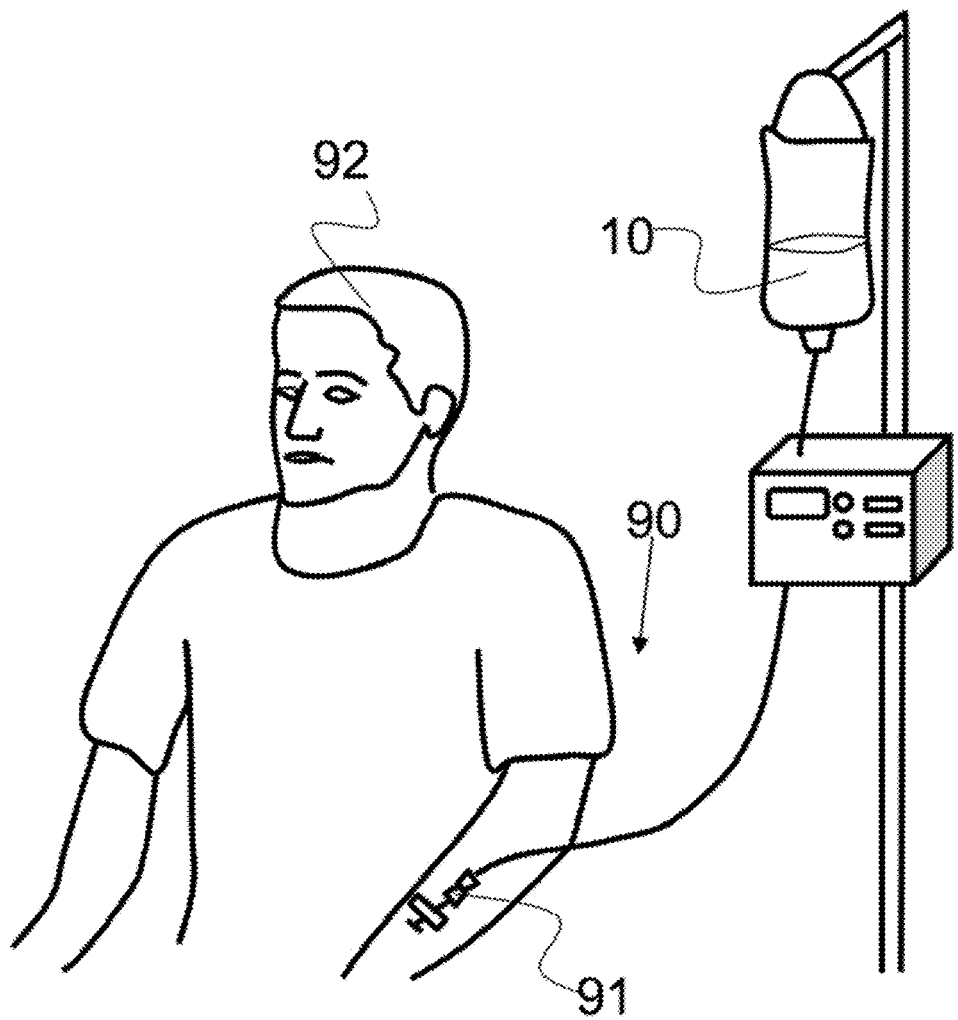

FIG. 22 shows an acellular amniotic derived composition being administered intravenously through a catheter.

Figure 23:
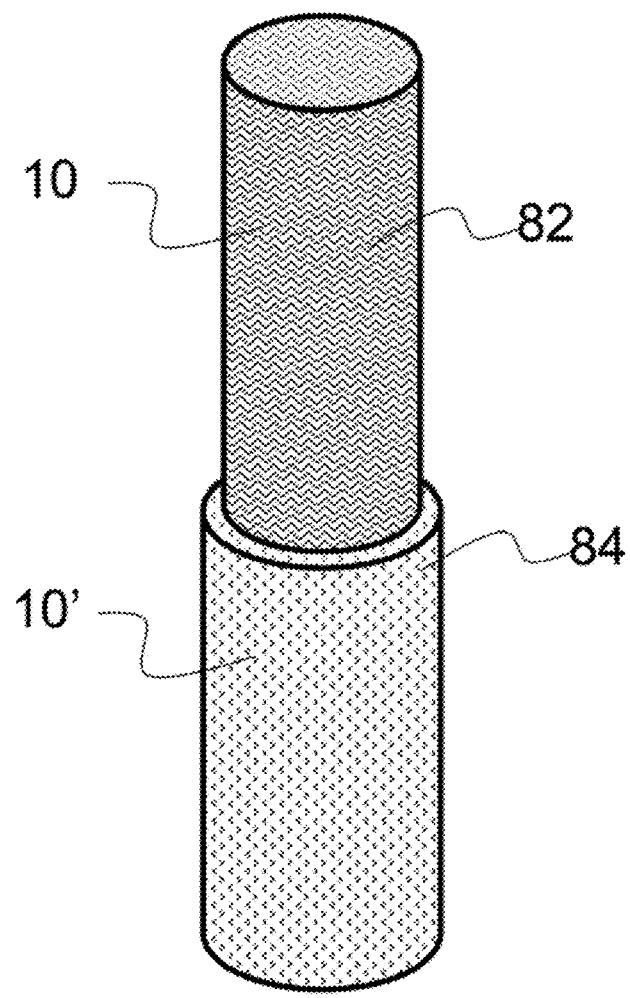

FIG. 23 shows a stent having an acellular amniotic derived composition configured thereon.

Figure 24:
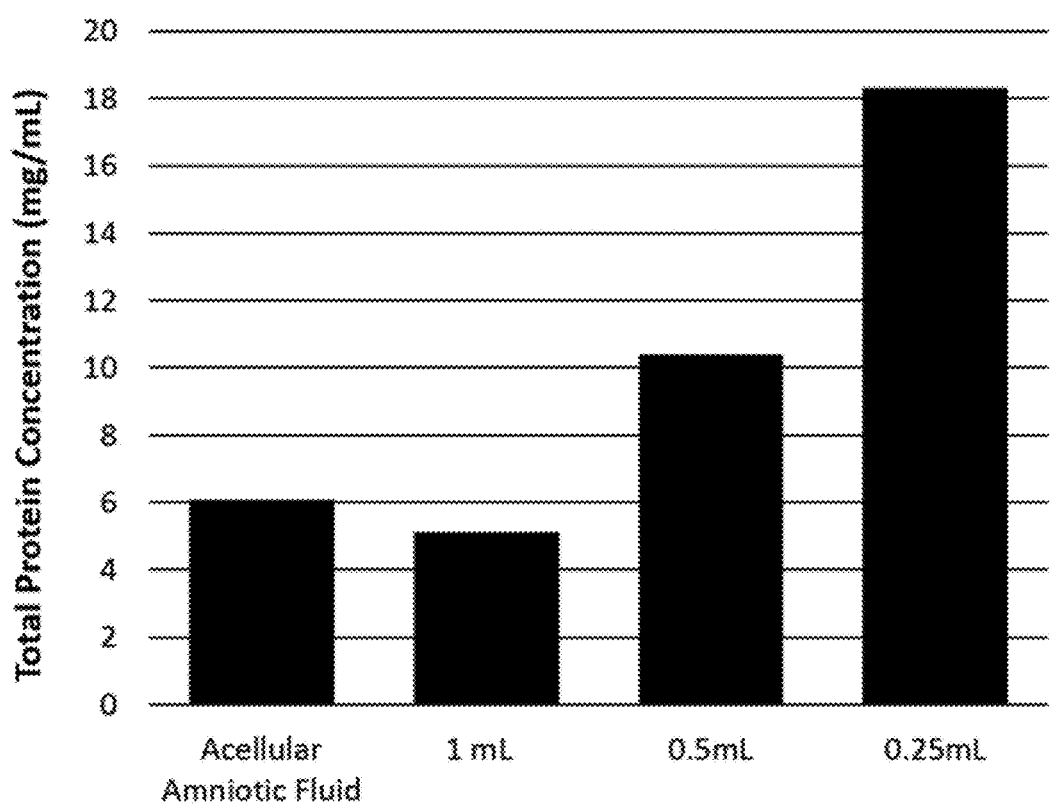

FIG. 24 shows a chart of data collected as part of Example 1.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1A the amniotic membrane surrounds a fetus in utero. As shown in FIG. 1B, the amniotic membrane comprises an amnion portion and a chorion portion. As described herein, the amnion portion may be separated from the chorion. In an exemplary embodiment, the epithelium, or inner most layer of the amniotic membrane, is removed and used to produce particles for the acellular amnion derived therapeutic composition, as described herein. The particles may consist essentially of the epithelium, consist essentially of the epithelium and base membrane, consist essentially of the epithelium, base membrane and compact layer, or consist essentially of epithelium, base membrane, compact layer, and fibroblast layer.

As shown in FIGS. 2A and 2B, the epithelium layer of the amniotic membrane 20 has a single layer of amniotic stem cells 46. The tissue around the amniotic stem cells may protect and enhance the viability of these stem cells when the epithelium is cryo-fractured to produce particles for the therapeutic composition.

As shown in FIG. 3A, an amniotic membrane 20 comprises a plurality of amniotic stem cells 46.

As shown in FIG. 3B, particles of cryo-fractured amniotic membrane particles 40 are on the order of 0.2 to 0.5 µm in size. The average particle size shown is less than 2 µm. There are no particles shown that are larger than 2 µm and substantially all of the particles are less than 1 µm in size. The SEM shows that the micronized amniotic membrane particles are irregularly shaped. As shown, some of the particles have a planar surface.

As shown in FIG. 4, a process to produce an acellular amnion derived therapeutic composition, as described herein, comprises the steps of cryo-fracturing amniotic membrane fragments to produce micronized amniotic membrane particles. As described, the amniotic membrane fragments may be cryo-fractured with a blunt object, such as a bar, that reduces shear and damage teethe particles. In a preferred embodiment, the fragments are cryo fractured with an object having substantially no sharp edges. The micronized particles are combined with any suitable carrier fluid to produce an acellular amnion derived therapeutic composition. In an exemplary embodiment, the micronized particles are dispersed in a fluid comprising amniotic fluid. The cells in the amniotic membrane may be destroyed prior to or after the process shown in FIG. 4, or between any of the steps.

As shown in FIG. 5, a process to produce an acellular amnion derived therapeutic composition, as described herein, comprises the steps of concentrating an amniotic fluid component comprising Plasma Lyte-A, available from Baxter Inc. An amniotic fluid may be processed in any suitable way to concentrate the amniotic fluid and components therein. For example, an amniotic fluid may be heated or allowed to evaporate, with or without vacuum, to concentrate the amniotic fluid. The cells in the amniotic fluid may be destroyed prior to or after the process shown in FIG. 5, or between any of the steps.

FIG. 6 shows a diagram of the anatomy and various organs within the body that may be treated with an acellular amnion derived therapeutic composition as described herein. An acellular amnion derived therapeutic composition, as described herein, may be introduced into any anatomy shown in FIG. 6 by direct injection, topical application, or transcatheter.

FIG. 7 shows a diagram of the circulatory system where an acellular amnion derived therapeutic composition may be introduced into the body through injection or transcatheter.

FIG. 8 shows an exemplary acellular amnion derived therapeutic composition 10 being drawn from an enclosure 70 by a syringe 80. The acellular amnion derived therapeutic composition comprises micronized particles 22 of amniotic membrane 20. The needle may be any suitable size, however in a preferred embodiment the needle is no larger than a 20 gauge needle.

As shown in FIG. 9, a syringe 80 is injecting an acellular amnion derived therapeutic composition 10 comprising micronized particles of amniotic membrane 22 dispersed in a fluid component 14 into the knee joint.

FIG. 10 shows a cross-sectional diagram of an eye and some of the treatment locations for an acellular amnion derived therapeutic composition, as described herein. For example, an acellular amnion derived therapeutic composition, as described herein, may be applied topically and/or injected into the iris, anterior chamber, lens, vitreous humor, cilliary muscle, cornea, extraocular muscle, sclera, choroid, retina and the like.

As shown in FIG. 11, a representation of an amniotic membrane 20 comprises pores 29 between the amniotic membrane tissue. This porosity may be imbibed with an acellular amnion derived therapeutic composition. In addition, an amniotic membrane may be stretched in one or more directions to tensilize the tissue. A tensilized amniotic membrane may have a higher matrix tensile strength than an original un-tensilized amniotic membrane. In addition, a plurality of layers of amniotic membrane may be utilized to build strength in one or more directions.

As shown in FIG. 12A, an amniotic membrane 20 has been stretched in one direction to form an elongated and more aligned amniotic tissue orientation. As shown in FIG. 12A, oriented tissue 23 is aligned horizontally and connecting tissue interconnects the oriented tissue. A tensilized amniotic membrane 21 may be stronger by unit weight in the oriented direction and may have a much higher elongation to break in the cross-oriented direction than a precursor amniotic membrane, before tensilizing. The tensilized amniotic membrane 21 may be stretched as much as 120% 150%, 175%, or 200% of the original membrane length. The amniotic membrane may neck or narrow in the opposing direction of stretch. A stretched or tensilized amniotic membrane may be stretched over a long period of time to minimize tissue fracture. For example, an amniotic membrane may have a low load applied and may be stretched over a period of 10 minutes or more, 30 minutes or more, 1 hour or more, 6 hours or more, 1 day or more, 2 days more and any range between and including the durations provided. In addition, an amniotic membrane may be stretched while being hydrated and/or submerged in amniotic fluid or a plasticizing fluid. An amniotic membrane may be cross-linked after being stretched. The load applied to tensilize an amniotic membrane may be a portion of the maximum tensile load required to fracture the amniotic membrane at a rate of 10 mm/second for a 25.4 mm by 15.24 cm sample having a 50.8 mm gap. For example, a tensilizing load applied may be no more than about 80%, no more than about 60%, no more than about 50%, or no more than about 25% of the maximum tensile load.

As shown in FIG. 12B, a first tensilized amniotic membrane 20 is configured at a 90 degree offset from a second amniotic membrane 20. This orientation of layering may provide for a much stronger therapeutic composite. In an alternative embodiment, a plurality of layers of tensilized amniotic membrane may be aligned with the oriented tissue of a first layer being aligned with the oriented tissue of a second layer. A matrix component or a therapeutic composite, as described herein, may consist essentially of tensilized amniotic membrane.

As shown in FIG. 13, an exemplary acellular amnion derived therapeutic composite 11 comprises an amniotic membrane 20 configured over a treatment location 18 in the tissue 19 of a subject. The matrix component 12 in this embodiment consists essentially of amniotic membrane 20.

As shown in FIG. 14, an exemplary acellular amnion derived therapeutic composite 11 comprises an amniotic membrane 20 and fluid component 14 configured over a treatment location 18. The fluid component 14 comprises micronized amniotic membrane particles 22 and amniotic fluid 43. Any suitable fluid carrier may be used to disperse the micronized amniotic membrane particles and/or amniotic fluid.

As shown in FIG. 15, an exemplary acellular amnion derived therapeutic composite 11 is configured over a treatment location 18 wherein the therapeutic composite comprises an acellular amniotic membrane 20 imbibed with a fluid component 14 and a cover layer 24 is configured there over. The matrix component 12 comprises a first matrix layer 30 and a second matrix layer 32. The second matrix layer is configured over said first matrix layer and comprises an overhang portion 36 that extends outside of the first matrix layer. The second matrix layer is attached to the tissue 19 by an attachment component 38, such as a staple, glue and/or sutures, for example. A matrix component, or a layer of a matrix component, may be configured to extend beyond a treatment location, whereby an outer area of the matrix component can be affixed to tissue. A cover layer may fully cover a first or under layer of matrix component or may only cover a portion of a layer thereunder. A cover layer may be a net or mesh or strands that extend across and over an under-layer, for example.

As shown in FIG. 16, an exemplary acellular amnion derived therapeutic composite 11 is configured over a treatment location 18. The acellular therapeutic composite 11 comprises a matrix component 12 comprising a first matrix layer 30 of amniotic membrane 20, a second matrix layer 32 of a fluid reservoir layer 25, and a third matrix layer 34 that is a cover layer 24. The fluid reservoir layer comprises a matrix having porosity containing a fluid component 14', as described herein. As shown, a first fluid component 14 is configured within the first matrix layer 30. It is to be noted that different compositions of a first and second fluid component may be configured in a matrix component 12.

As shown in FIG. 17, an acellular amnion derived therapeutic composite 11 is configured over a treatment location 18 wherein the matrix component 12 comprises a first matrix layer 30 of amniotic membrane 20 imbibed with fluid component 14 and a second matrix layer 32 that is a support layer 39 comprising bioresorbable material 26. The support layer may be substantially impermeable to the fluid component configured in the first matrix component that is proximate a treatment location. In addition, an outer surface 52 of a matrix component 12, or the surface facing away a treatment location, may be hydrophobic to reduce fluid ingress into the therapeutic composite. Bodily fluid ingress into a therapeutic composite may dilute a fluid component comprised therein.

As shown in FIG. 18, an exemplary acellular amnion derived therapeutic composite 11 is configured over a treatment location 18 wherein the matrix component 12 comprises a first matrix layer 30 of amniotic membrane 20 imbibed with fluid component 14, a second matrix layer 32 that is a support layer 39 and a third matrix layer 34 that comprises amniotic membrane 20. A support layer is configured between amniotic membranes in this embodiment. As described herein, a matrix component may be provided with multiple layers attached and ready for orientation on a treatment location, or a plurality of matrix components may be applied, one after another, during the treatment procedure.

As shown in FIG. 19, an exemplary acellular amnion derived therapeutic composite 11 is configured around a ureter and a fluid component 14 is being injected therein. This type of procedure may reduce and/or eliminate strictures. A matrix component may be a sheet of material having a substantially planar top and bottom surface and substantially uniform thickness therebetween. A sheet of matrix composite may be supple and may be configured around a cylindrical treatment location, such as a portion of the urinary or digestive system. In another embodiment, a matrix component sheet is applied externally over a treatment location in a patient's dermal tissue. It is to be understood that a composition comprising viable cells may be injected into or otherwise placed into contact with an acellular amnion derived therapeutic composite, as described herein. For example, the syringe 80 shown in FIG. 19 may comprise live viable stem cells that are injected into an exemplary acellular amnion derived therapeutic composite 11. The stem cells may be any suitable type of stem cells.

As shown in FIG. 20, a wound on a diabetic person's foot has a length of approximately 11 mm and width of approximately 7 mm. An acellular amnion derived therapeutic composite of amniotic membrane may be placed over the wound and a fluid component comprising micronized amniotic membrane and a concentrated amniotic fluid may be applied topically. Stem cells derived from the patient's stromal vascular fraction may be applied to the treatment location as well.

As shown in FIG. 21, a patient has an osteochondral defect in an ankle, with some bone degradation. An acellular amnion derived therapeutic composite may be applied over the defect and an acellular amnion derived therapeutic fluid component may then be applied to the treatment site.

As shown in FIG. 22, a patient 92 is receiving an intravenous treatment 90 of an acellular amnion derived composition 10, as described herein. The acellular amnion derived composition 10 is being introduced intravenously through a catheter 91.

As shown in FIG. 23, a stent 82 having a stent covering 84 on a portion of the stent comprises an acellular amnion derived composition 10. As described herein, an acellular amnion derived composition may be coated onto a metal stent 82 or coated onto or imbibed into a stent covering, such as an expanded fluoropolymer material. Expanded PTFE is often used in covered stent applications and an acellular amnion derived composition may be coated onto or imbibed into the porosity, or pores of the expanded PTFE. In another embodiment, an amniotic membrane is configured as a stent covering and an acellular amnion derived composition may be combined with the amniotic membrane to form a stent covering.

EXAMPLE 1

Three 1 mL samples of acellular amniotic fluid were lyophilized under gentle vacuum. The resulting was subsequently gradually reconstituted in 1 ml, 0.5 ml, or 0.25 ml of Plasma-Lyte A at 4° C. avoiding mechanical stress. Total protein concentration prior to lyophilization and in reconstituted samples was measured using the NanoDrop 8000 spectrophotometer platform. Total protein concentration in the acellular amniotic fluid prior to lyophilization (Acellular Amniotic Fluid), and reconstituted in 1 mL, 0.5 ml, and 0.25 mL was 6.24 mg/mL, 5.1 mg/mL, 10.41 mg/mL, and 18.31 mg/mL, respectively, as shown in FIG. 24. Total protein concentration in the samples reconstituted in 1 mL, 0.5 mL, and 0.25 mL of Plasma Lyte-A were 84%, 172%, and 302%, respectively, as compared to the non-lyophilized acellular amniotic fluid.

DEFINITIONS

An acellular amnion derived composition is a material derived from amnion material, including amniotic membrane and amniotic fluid, but contains essentially no live amniotic cells. In an exemplary embodiment, an amnion derived acellular composition comprises no live or active amniotic derived cells including amniotic fluid and amniotic membrane cells. In yet another embodiment, an acellular amnion derived therapeutic composition comprises essentially no intact amniotic derived cells. As described herein, during the micronizing of the amniotic membrane, cells may be fractured leaving cell fragments and essentially no intact cells.

An acellular material, as used herein, is defined as a material having essentially no viable cells wherein no more than 1% of the total number of cells in the material are viable. In an exemplary embodiment, an acellular composition contains no viable cells. In an exemplary embodiment, an acellular composition is essentially cell free. Essentially cell free, as used herein, is defined as a composition that contains essentially no intact cells, or no more than five percent no more than three percent, no more than two percent, or no more than one percent of an original intact cell concentration, or no more than about 750,000 intact cells per ml of material, no more than about 450,000 intact cells per ml of material, no more than about 300,000 intact cells per ml of material, or no more than about 150,000 intact cells per ml of material. An essentially cell free material may contain cell fragments that have been destroyed through cryo-fracturing, for example.

Micronized placental tissue particles, as used herein, is defined as particles derived from placenta including amniotic membrane (amnion), chorion, Wharton's Jelly, umbilical cord, and the like. Amniotic membrane particles may be preferred for therapeutics effectiveness. Placental tissue may be micronized to have an average particle size of no more than about 1000 um, and preferably no more than about 100 um, and may have an average particle size of no more than about 75 um, no more than about 50 um, no more than about 25 um, no more than about 10 um and any range between and including the average particle sizes provided. Particle size may be measured by analysis of scanning electron micrographs. Micronized placental tissue particles may be formed through any suitable method including, but not limited to, cryogenic fracturing, application of heat and pressure, sonication and/or enzyme digestion.

Amniotic fluid may be decellularized to remove a portion of the cells through centrifugation, for example. A decellularized amniotic fluid may be an essentially cell free amniotic fluid obtained through centrifugation, filtration, or other process to remove essentially all of the cells and/or cell debris and may contain essentially no intact cells, or no more than about five percent, no more than three percent, no more than two percent, or no more than one percent of an original intact cell concentration, or no more than about 750,000 intact cells per ml of material, no more than about 450,000 intact cells per ml of material, no more than about 300,000 intact cells per ml of material or no more than about 150,000 intact cells per ml of material.

An amniotic cell, as used herein is a cell derived from amniotic fluid or amniotic membrane.

An intact cell, as used herein, is a cell that is viable or non-viable and retains an original shape and has not been ruptured or split into two or more pieces.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of topically treating an external body treatment location comprising the steps of:
   a) providing a therapeutic composition comprising:
      i. acellular amniotic membrane particles;
      ii. a carrier fluid comprising an acellular amniotic fluid;
   wherein the acellular amniotic membrane particles consist essentially of micronized amniotic membrane; and
   wherein the therapeutic composition is essentially free of any viable amniotic membrane cells or viable amniotic fluid cells;
   b) applying the therapeutic composition topically to said external body treatment location.

2. The method of claim 1, wherein the t treatment location is skin.

3. The method of claim 1, wherein the treatment location is the skin the method of treating is for atopic dermatitis.

4. The method of claim 1, wherein the treatment location is hair or a hair follicle.

5. The method of claim 1, wherein the treatment location is an ophthalmic lesion.

6. The method of claim 1, wherein the treatment location is a wound.

7. The method of claim 1, wherein the treatment location is an eye.

8. The method of claim 1, wherein the treatment location is an ear.

9. The method of claim 1, wherein the treatment location is a mouth.

10. The method of claim 1, wherein the treatment location is a mucosal membrane.

11. The method of claim 1, wherein the treatment location is a first degree burn, a second degree burn, or a third degree burn.

12. The method of claim 1, wherein the treatment location is keloid scar, surgical or traumatic induced scar.

13. The method of claim 1, wherein the therapeutic composition comprises at least one of an oil or wax and has a viscosity of at least 5k cps.

14. The method of claim 1, wherein the therapeutic comp an is a cream.

15. The method of claim 1, wherein the therapeutic composition is a lotion.

16. The method of claim 1, wherein the therapeutic composition is an ointment.

17. The, method of claim 1, wherein the therapeutic composition is a gel.

18. A method of treating a treatment location comprising the steps of:
   a. providing a therapeutic composition comprising:
      i. acellular amniotic membrane particles;
      ii. a carrier fluid comprising an acellular amniotic fluid;
   wherein the acellular amniotic membrane particles consist essentially of l icronized amniotic membrane; and
   wherein the therapeutic composition is essentially free of any viable amniotic membrane cells or viable amniotic fluid cells;
   b. providing a syringe containing said therapeutic composition;
   c. applying the therapeutic composition via injection with the syringe to reatment location.

19. The method according to claim 18, wherein the treatment location is an articular joint.

20. The method according to claim 18, wherein the treatment location is a muscle.

21. The method according to claim 18, wherein the treatment location is an organ.

22. The method according to claim 18, wherein the treatment location is an eye and associated ophthalmic structures.

23. The method according to claim 18, wherein the treatytreatment location is a soft tissue.

24. The method accordin to claim 18, wherein the treatment location is an artery or a vein.

25. The method according to claim 18, wherein the treatment location is a tooth.

26. A method of intravenously or intra-arterial or cerebrospinal treating a patient with a therapeutic composition comprising the steps of:
   a) providing a therapeutic composition comprising:
      i. acellular amniotic membrane particles;
      ii. a carrier fluid comprising an acellular amniotic fluid;
   wherein the acellular amniotic membrane particles consist essentially of micronized amniotic membrane; and
   wherein, the therapeutic composition is essentially free of any viable amniotic membrane cells, or viable amniotic fluid cells;
   b) providing an intravenous, an intra-arterial or cerebrospinal system comprising:
      i. a venous, an arterial or a cerebral access port, respectively; and
      ii. a treatment solution reservoir comprising said therapeutic composition;
   c) coupling the access port to a patient's venous, arterial, cardiac or cerebrospinal system;
   d) dispensing the treatment composition into the patient's venous, arterial, cardiac or cerebrospinal system to treat the patient with the therapeutic composition intravenously.

27. A method of claim 26, wherein the therapeutic composition is introduced into a pulmonary artery.

28. A method of claim 26, wherein the therapeutic composition is introduced through a central venous catheter.

29. A method of claim 26, wherein the therapeutic composition is introduced through a trans-bronchial catheter.

30. A method of claim 26, wherein the therapeutic composition is introduced though a peripheral venous catheter.

31. A method of treating a treatment location intraoperatively with a therapeutic composition comprising the steps of:
   a. providing a therapeutic composition comprising:
      i. acellular amniotic membrane particles;
      ii. a carrier fluid comprising an acellular amniotic fluid;
   wherein the acellular amniotic membrane particles consist essentially of micronized amniotic membrane; and
   wherein the therapeutic composition is essentially free of any viable amniotic membrane or viable amniotic fluid cells;
   b) applying the therapeutic composition intraoperatively to a treatment location.

32. The method of claim 31, wherein the treatment location in an organ.

33. The method of claim 31, wherein the treatment location is an operative incision.

34. The method of claim 31, wherein the step of applying the therapeutic composition comprises topically applying the therapeutic composition to a treatment location.

35. The method of claim 31, wherein the step of applying the therapeutic composition comprises injecting the therapeutic composition with a syringe into a treatment location.

36. A method of orally treating a patient with a therapeutic composition, comprising the steps of:
   a. providing a therapeutic composition comprising:
      i. acellular amniotic membrane particles;
      ii. a carrier fluid comprising an acellular amniotic fluid;
   wherein the acellular amniotic membrane particles consist essentially of micronized amniotic membrane; and
      iii. wherein the therapeutic composition is essentially free of any viable amniotic membrane cells or viable amniotic fluid cells
   b. administering the therapeutic composition orally.

37. The method of claim 36, wherein the therapeutic composition is a liquid, a capsule, or a tablet.

* * * * *